US012559490B2

(12) United States Patent
Sun et al.

(10) Patent No.: US 12,559,490 B2
(45) Date of Patent: *Feb. 24, 2026

(54) COMPOSITIONS AND METHODS FOR MODULATING HAIR GROWTH

(71) Applicants: The Regents of the University of California, Oakland, CA (US); Pelage Pharmaceuticals, Inc., Los Angeles, CA (US)

(72) Inventors: Daniel L. Sun, Los Angeles, CA (US); Michael E. Jung, Los Angeles, CA (US); Daniel W. Gil, Los Angeles, CA (US)

(73) Assignees: The Regents of the University of California, Oakland, CA (US); Pelage Pharmaceuticals, Inc., Los Angeles, CA (US)

(*) Notice: Subject to any disclaimer, the term of this patent is extended or adjusted under 35 U.S.C. 154(b) by 476 days.

This patent is subject to a terminal disclaimer.

(21) Appl. No.: 18/013,803

(22) PCT Filed: Jun. 29, 2021

(86) PCT No.: PCT/US2021/039502

§ 371 (c)(1),
(2) Date: Dec. 29, 2022

(87) PCT Pub. No.: WO2022/006040

PCT Pub. Date: Jan. 6, 2022

(65) Prior Publication Data

US 2023/0322765 A1 Oct. 12, 2023

Related U.S. Application Data

(60) Provisional application No. 63/046,629, filed on Jun. 30, 2020.

(51) Int. Cl.
*C07D 471/04* (2006.01)

(52) U.S. Cl.
CPC .................................. *C07D 471/04* (2013.01)

(58) Field of Classification Search
CPC .................................. C07D 471/04
USPC .................................. 514/300
See application file for complete search history.

(56) References Cited

U.S. PATENT DOCUMENTS

| | | | |
|---|---|---|---|
| 3,524,860 | A | 8/1970 | Albertson |
| 5,124,354 | A | 6/1992 | Green |
| 5,397,787 | A | 3/1995 | Buzzetti et al. |
| 5,663,346 | A | 9/1997 | Buzzetti et al. |
| 6,541,507 | B1 | 4/2003 | Dalko et al. |
| 8,470,849 | B2 | 6/2013 | Carniato et al. |
| 9,499,551 | B2 | 11/2016 | Jacobsen et al. |
| 11,213,513 | B2 | 1/2022 | Lowry et al. |
| 11,312,714 | B2 | 4/2022 | Lowry et al. |
| 11,472,804 | B2 | 10/2022 | Lowry et al. |
| 11,787,804 | B2 | 10/2023 | Lowry et al. |
| 12,227,503 | B2 | 2/2025 | Lowry et al. |
| 2008/0064765 | A1 | 3/2008 | Birnbaum |
| 2009/0269418 | A1 | 10/2009 | Albeck et al. |
| 2010/0305187 | A1 | 12/2010 | Guelow et al. |
| 2011/0028460 | A1 | 2/2011 | Kisak et al. |
| 2013/0023587 | A1 | 1/2013 | Schroeder et al. |
| 2013/0337031 | A1 | 12/2013 | Kisak et al. |
| 2015/0140071 | A1 | 5/2015 | Rajasekaran |
| 2020/0030289 | A1 | 1/2020 | Lowry et al. |
| 2020/0157093 | A1 | 5/2020 | Lowry et al. |
| 2020/0253917 | A1 | 8/2020 | Lowry et al. |
| 2022/0048908 | A1 | 2/2022 | Lowry et al. |
| 2022/0153738 | A1 | 5/2022 | Lowry et al. |
| 2023/0103693 | A1 | 4/2023 | Jung et al. |
| 2023/0114220 | A1 | 4/2023 | Lowry et al. |
| 2023/0322765 | A1 | 10/2023 | Sun et al. |
| 2024/0025895 | A1 | 1/2024 | Lowry et al. |
| 2024/0327400 | A1* | 10/2024 | Sun ...................... C07D 471/04 |
| 2025/0145626 | A1* | 5/2025 | Sun ...................... A61P 17/14 |
| 2025/0163045 | A1 | 5/2025 | Sun et al. |

FOREIGN PATENT DOCUMENTS

| | | | |
|---|---|---|---|
| CN | 1093707 | A | 10/1994 |
| CN | 106880693 | A | 6/2017 |
| DE | 3601285 | A1 | 7/1987 |
| EP | 0403238 | A2 | 12/1990 |
| EP | 0780389 | A1 | 6/1997 |
| EP | 1068858 | A1 | 1/2001 |
| JP | S 59-161357 | A | 9/1984 |
| KR | 2004/0029371 | A | 4/2004 |
| WO | WO-9200057 | A1 | 1/1992 |
| WO | WO-1992/007839 | A1 | 5/1992 |
| WO | WO-96/00226 | A1 | 1/1996 |

(Continued)

OTHER PUBLICATIONS

U.S. Appl. No. 16/488,451, Issued.
U.S. Appl. No. 16/627,630, Issued.
U.S. Appl. No. 17/584,091, Issued.
U.S. Appl. No. 17/847,980, Pending.
U.S. Appl. No. 17/420,293, Pending.
U.S. Appl. No. 18/013,808, Pending.
Valeur et al., "Structure-based design of 7-azaindole-pyrrolidine amides as inhibitors of 11β-hydroxysteroid dehydrogenase type I." Bioorganic & medicinal chemistry letters 22.18 (2012): 5909-5914.
Khan et al., "Arylindoles. I. Synthesis of some N-arylindoles." Chemical and Pharmaceutical Bulletin 25.11 (1977): 3110-3114.

(Continued)

*Primary Examiner* — Niloofar Rahmani
(74) *Attorney, Agent, or Firm* — Foley Hoag LLP; David P. Halstead; Alexander J. Chatterley

(57) ABSTRACT

The present disclosure relates to novel compounds that are capable of inhibiting the mitochondrial pyruvate carrier and promoting hair growth. The disclosure further relates to methods of promoting hair growth or treating conditions or disorders affecting hair growth, such as baldness or alopecia.

18 Claims, 1 Drawing Sheet

(56) References Cited

FOREIGN PATENT DOCUMENTS

| | | | |
|---|---|---|---|
| WO | WO-0162237 | A2 | 8/2001 |
| WO | WO-03/007951 | A1 | 1/2003 |
| WO | WO-2004/080481 | A1 | 9/2004 |
| WO | WO-2005/051908 | A1 | 6/2005 |
| WO | WO-2005/054247 | A1 | 6/2005 |
| WO | WO-2005/123664 | A2 | 12/2005 |
| WO | WO-2005/123731 | A2 | 12/2005 |
| WO | WO-2007/002433 | A1 | 1/2007 |
| WO | WO-2007/068418 | A1 | 6/2007 |
| WO | WO-2007/099396 | A2 | 9/2007 |
| WO | WO-2008/028118 | A1 | 3/2008 |
| WO | WO-2009/059666 | A1 | 5/2009 |
| WO | WO-2010/001169 | A2 | 1/2010 |
| WO | WO-2012/078649 | A1 | 6/2012 |
| WO | WO-2013/128465 | A1 | 9/2013 |
| WO | WO-2013/169956 | A2 | 11/2013 |
| WO | WO-2013/188554 | A1 | 12/2013 |
| WO | WO-2014/113467 | A1 | 7/2014 |
| WO | WO-2014/207213 | A1 | 12/2014 |
| WO | WO-2015/042053 | A1 | 3/2015 |
| WO | WO-2015/049365 | A2 | 4/2015 |
| WO | WO-2015/112854 | A1 | 7/2015 |
| WO | WO-2017/196936 | A1 | 11/2017 |
| WO | WO-2018/039612 | A1 | 3/2018 |
| WO | WO-2018/039615 | A1 | 3/2018 |
| WO | WO-2019/006359 | A1 | 1/2019 |
| WO | WO-2020/142413 | A1 | 7/2020 |
| WO | WO-2021/127482 | A1 | 6/2021 |
| WO | WO-2022/006039 | A1 | 1/2022 |
| WO | WO-2022/006040 | A1 | 1/2022 |
| WO | WO-2021/127482 | A8 | 6/2022 |

OTHER PUBLICATIONS

U.S. Appl. No. 17/786,986, Pending.
U.S. Appl. No. 17/847,980, Issued.
U.S. Appl. No. 18/241,583, Allowed.
Extended European Search Report for Application No. 28132522.3 dated Dec. 11, 2023.
Extended European Search Report for EP Application No. 21832044.8 dated Dec. 7, 2023.
Zhou et al., "Structure-based discovery of new maternal embryonic leucine zipper kinase inhibitors", Organic & Biomolecular Chemistry, vol. 16, No. 9, pp. 1489-1495 (2018).
U.S. Appl. No. 18/241,583, Pending.
CAS Registry No. 139336-32-6: Entered STN: Feb. 28, 1992.
CAS Registry No. 861644-67-9: Entered STN: Aug. 8, 2005.
CAS Registry No. 96618-51-8: Entered STN: Jan. 3, 1985.
Fairhurst et al., "A synthesis of CIS-α, β-unsaturated nitriles by kinetically controlled decarboxylation" Tetrahedron Letters, No. 22, pp. 3843-3844 (1975).
Harisha et al., "Reaction of 3-arylidenepropenoic acid derivatives with triethylamine and other amines; unexpected reductions and vinylogations" Tetrahedron Letters, No. 72, pp. 2880-2889 (2016).
Salin et al., "Phosphine-catalyzed addition of P(O)-H compounds to ethyl phenylpropiolate" Tetrahedron Letters, No. 56, pp. 6282-6286 (2015).
Shelke et al., "An Efficient Synthesis of 5-Arylidene-2,4-ThiazolidinedioneCatalyzed by Boric acid in Aqueous media under Ultrasound-Irradiation" Chemistry and Biology Interface, vol. 6, No. 6, pp. 410-415 (2016).
U.S. Appl. No. 17/420,293, Issued.
U.S. Appl. No. 18/013,808, Issued.
Date et al., "A Highly Regio- and Stereoselective Vinylogous Horner-Wadsworth-Emmons Route to Densely Substituted 1, 3-Butadienes", Angewandte Chemie International Edition 46.3: 386-388 (2007).
Extended European Search Report for EP Application No. 20903755.5 dated Jan. 9, 2024.
Gordon et al., "Development of Second-Generation Indole-Based Dynamin GTPase Inhibitors" Journal of Medicinal Chemistry, vol. 56, p. 46-59 (2013).
Krawyczyk et al., "Knoevenagel Reaction of Diethylphosphonoacetic Acid: A Facile Route to Diethyl (E)-2-Arylvinylphosphonates" Synthesis, No. 17, p. 2887-2896 (2005).
Moriya et al., "Preparation and reactions of 3-(aminomethylene)-3H-indoles", Chemical and Pharmaceutical Bulletin 28.6: 1711-1721 (1980).
Silverman et al., "The Organic Chemistry of Drug Design and Drug Action" translated by GUO Zongru, Chemical Industry Press, 1st edition, pp. 17-23, Jan. 31, 2008.
Amin et al., "Exploring structural requirements of unconventional Knoevenagel-type indole derivatives as anticancer agents through comparative QSAR modeling approaches," Can J Chemistry, 94(7):637-644 (2016).
Brennan et al., "The Allosteric Site on SHP2's Protein Tyrosine Phosphatase Domain is Targetable with Druglike Small Molecules," ACS Omega, 3(11): 15763-15770 (2018).
CAS Registry No. 891610-48-3: CA Index Name "2-Propenamide, 2-cyano-3-[1-[3-(trifluoromethyl)phenyl]methyl]-1H-indol-3-yl]-" STN International: 3 pages (2006).
CAS Registry No. 1332531-33-5, Entered STN: Sep. 15, 2011.
CAS Registry No. 891614-21-4, Entered STN: Jul. 10, 2006.
CAS Registry No. 907553-40-6, Entered STN: Sep. 19, 2006.
CAS Registry No. 925549-16-2, Entered STN: Mar. 8, 2007.
CAS Registry No. 374601-67-9, Entered STN: Dec. 10, 2001.
CAS Registry No. 677327-34-3; CA Index Name: 2-Propenamide, 2-cyano-N-ethyl-3-(1H-pyrrolo[2,3-b]pyridin-3-yl)-; Entered STN: Apr. 28, 2004.
CAS Registry No. 94331-28-9. Jan. 21, 1985.
CAS Registry No. 1025594-30-2, Entered STN:Jun. 5, 2008.
CAS Registry No. 1232821-01-0, Entered STN:Jul. 19, 2010.
CAS Registry No. 1246086-21-4, Entered STN:Oct. 12, 2010.
CAS Registry No. 1360583-75-0, Entered STN:Mar. 9, 2012.
CAS Registry No. 1360583-78-3, Entered STN:Mar. 9, 2012.
CAS Registry No. 1417368-01-4, Entered STN:Jan. 23, 2013.
CAS Registry No. 1993738-37-6, Entered STN: Sep. 16, 2016.
CAS Registry No. 1993795-68-8, Entered STN:Sep. 16, 2016.
CAS Registry No. 2022941-63-3, Entered STN:Nov. 2, 2016.
CAS Registry No. 2094959-90-5, Entered STN:May 5, 2017.
CAS Registry No. 677327-34-3, Entered STN:Apr. 28, 2004.
CAS Registry No. 895303-82-9, Entered STN:Jul. 23, 2006.
CAS Registry No. 895304-22-0, Entered STN:Jul. 23, 2006.
CAS Registry No. 904141-89-5, Entered STN: Aug. 24, 2006.
Castilho et al., "mTOR Mediates Wnt-Induced Epidermal Stem Cell Exhaustion and Aging," Cell Stem Cell, 5(3): 279-289 (25 pages)(2009).
Choi et al., "The effect of cilostazol, a phosphodiesterase 3 (PDE3) inhibitor, on human hair growth with the dual promoting mechanisms," Journal of Dermatological Science, 91: 60-68 (2018).
El Maatougui et al., "Supported TBD-Assisted Solution Phase Diversification of Formyl-Aza-Heterocycles Through Alkylation-Knoevenagel One Pot Sequences," Combinatorial Chemistry & High Throughput Screening, 14: 570-582 (2011).
Extended European Search Report for EP Application No. 17844520.1 mailed Jul. 21, 2020.
Extended European Search Report for EP Application No. 18823621 mailed Jun. 15, 2021.
Extended European Search Report for EP Application No. 18862674.1 dated Jun. 18, 20201.
Fischer et al., "Effect of caffeine and testosterone on the proliferation of human hair follicles in vitro ," International Journal of Dermatology, 46: 27-35 (2007).
Flores et al., "Inhibition of pyruvate oxidation as a versatile stimulator of the hair cycle in models of alopecia," Experimental Dermatology, 30: 448-456 (2021).
Flores et al., "Lactate dehydrogenase activity drives hair follicle stem cell activation," Nature Cell Biology, 19(9): 1017-1026 ( 2017).
Hickey et al., "Demodectic Mange in a Tamarin (*Saguinus geoffroyi*) 1,2," Laboratory Animal Science, American Associate for Laboratory Animal Science, 33(1): 192-193 (1983).

(56) References Cited

OTHER PUBLICATIONS

Hong et al., "Synthesis of double D-A branched organic dyes employing indole and phenoxazine as donors for efficient DSSCs," Tetrahedron, 70(36): 6296-6302 (2014).
International Preliminary Report on Patentability for International Application No. PCT/US2018/040385 mailed Dec. 31, 2019.
International Search Report and Written Opinion for International Application No. PCT/US2017/048701 dated Nov. 6, 2017.
International Search Report and Written Opinion for International Application No. PCT/US2018/040385 dated Oct. 21, 2018.
International Search Report and Written Opinion for International Application No. PCT/US2018/053351 mailed Dec. 31, 2018.
International Search Report and Written Opinion for International Application No. PCT/US2019/068905 dated Apr. 6, 2020.
International Search Report and Written Opinion for International Application No. PCT/US2020/066078 dated Mar. 25, 2021.
International Search Report and Written Opinion for International Application No. PCT/US2021/039501 mailed Sep. 30, 2021.
International Search Report and Written Opinion for International Application No. PCT/US2021/039502 mailed Sep. 30, 2021.
Issue Notification for U.S. Appl. No. 16/627,630 dated Apr. 6, 2022.
Jelinek et al., "Mapping Metabolism: Monitoring Lactate Dehydrogenase Activity Directly in Tissue," Journal of Visualized Experiments, 136: 57760 (2018).
Keren et al., "The PDE4 inhibitor, apremilast, suppresses experimentally induced alopecia areata in human skin in vivo," Journal of Dermatological Science, 77: 71-81 (2015).
Khan et al., "Arylindoles. II. N-Arylindole-3-carboxaldehydes and Their Derivatives," Chemical and Pharmaceutical Bulletin, 27(2): 528-531 (1979).
Liu et al., "Development of Novel Mitochondrial Pyruvate Carrier Inhibitors to Treat Hair Loss," Joournal of Medicinal Chemistry, 64: 2046-2063 (2021).
Liu et al., "Identification of novel thiadiazoloacrylamide analogues as inhibitors of dengue-2 virus NS2B/NS3 protease," Bioorg Med Chem, 22(22):6344-6352 (2014).
Magar et al., "Synthesis of Some Novel 3-Substituted Indole Derivatives Using Polyamine Functionalized Heterogeneous Catalyst," Journal of Heterocyclic Chemistry, 52(6): 1684-1692 (2015).
McCommis et al., "Mitochondrial pyruvate transport: a historical perspective and future research directions," Biochem J, 466(3):443-454 (2015).
Miranda et al., "Topical Inhibition of the Electron Transport Chain Can Stimulate the Hair Cycle," Journal of Investigative Dermatology, 138(4):9680972 (2017).
Miranda et al., "Topical Inhibition of the Electron Transport Chain Can Stimulate the Hair Cycle," Journal of Investigative Dermatology, 138: 968-972 (2018).
Notice of Allowance for U.S. Appl. No. 17/584,091 dated Apr. 14, 2022.
Partial Supplementary European Search Report for EP Application No. EP 18823621 dated Mar. 15, 2021.
PubChem CID 6438504; "2-Cyano-3-(1-phenylindol-3-yl)acrylate," National Library of Medicine: 18 pages (Create date Apr. 28, 2006).
Sarifakioglu., "Determination of the sildenafil effect on alopecia areata in childhood: An open-pilot comparison study," Journal of Dermatological Treatment, 17(4): 235-237 (2006).
Shan et al., "Phenanthroline-tBuOK Promoted Intramolecular C-H Arylation of Indoles with ArI under Transition-Metal-Free Conditions," Organic Letters, 20(24): 7898-7901 (2018).
Shearman et al., "The concentration of the mitochondrial pyruvate carrier in rat liver and heart mitochondria determined with a-cyano-β-(1-phenylindol-3-yl)acrylate," Biochemical Journal 223(3): 673-676 (1984).
Starosyla et al., "Discovery of novel protein kinase FGFR1 inhibitors using pharmacophore modeling," Ukrainica Bioorganica Acta, 13(1): 13-20 w/ English Abstract (2015).
Taylor et al., "Src tyrosine kinsase activity in rat thecal—interstitial cells and mouse TM3 Leydig cells is positively associated with cAMP-specific phosphodiesterase activity," Molecular and Cellular Endocrinology, 126: 91-100 (1997).
Valdenaire et al., "Evolution of novel tricyclic CRTh2 receptor antagonists from a (E)-2-cyano-3-(1H-indol-3-yl)acrylamide scaffold," Bioorganic & Medicinal Chemistry Letters, 23(4): 944-948 (2013).
Vishnyakova et al., "Possible role of autophagy activation in stimulation of regeneration," Mol Biol, 47(5):692-700 (2013).
Wang et al., "Oxidative stress and substance P mediate psychological stress-induced autophagy and delay of hair growth in mice," Arch. Dermatol. Res. 307: 171-181 (2015).
Yakhontov et al., "Pyrrolo[2,3-b]pyridine derivatives (7-azaindoles) viii. Synthesis and some reactions of 4-methyl-1-phenyl-1h-4-methyl-1-phynyl-1 h-pyrrol0[2,3-b]pyridine-3-carboxaldehydel," All-Union Chem Pharma Res Int, translated from Zhurnal Obshchei Khimii 34(8):2603-2610 (1964).
STN Registry Database, RN 302562-57-8, entered Nov. 13, 2000.
STN Registry Database, RN 302562-58-9, entered Nov. 13, 2000.
STN Registry Database, RN 302825-78-1, entered Nov. 14, 2000.
STN Registry Database, RN 303202-38-2, entered Nov. 20, 2000.
STN Registry Database, RN 327076-80-2, entered Mar. 14, 2001.
STN Registry Database, RN 327076-81-3, entered Mar. 14, 2001.
STN Registry Database, RN 327076-82-4, entered Mar. 14, 2001.
STN Registry Database, RN 327076-84-6, entered Mar. 14, 2001.
STN Registry Database, RN 340212-10-4, entered Jun. 10, 2001.
STN Registry Database, RN 367469-20-3, entered Nov. 7, 2001.
STN Registry Database, RN 372973-07-4, entered Dec. 3, 2001.
STN Registry Database, RN 374092-98-5, entered Dec. 6, 2001.
STN Registry Database, RN 374601-46-4, entered Dec. 10, 2001.
STN Registry Database, RN 374601-67-9, entered Dec. 10, 2001.
STN Registry Database, RN 374697-43-5, entered Dec. 11, 2001.
STN Registry Database, RN 444567-77-5, entered Nov. 1, 2004.
STN Registry Database, RN 524732-67-0, entered Jun. 3, 2003.
STN Registry Database, RN 663203-03-0, entered Mar. 15, 2004.
STN Registry Database, RN 675864-84-3, entered Apr. 16, 2004.
STN Registry Database, RN 773082-62-5, entered Nov. 1, 2004.
STN Registry Database, RN 780812-59-1, entered Nov. 15, 2004.
STN Registry Database, RN 885523-21-7, entered May 25, 2006.
STN Registry Database, RN 890353-24-9, entered Jul. 3, 2006.
STN Registry Database, RN 890353-32-9, entered Jul. 3, 2006.
STN Registry Database, RN 891362-96-2, entered Jul. 10, 2006.
STN Registry Database, RN 891363-10-3, entered Jul. 10, 2006.
STN Registry Database, RN 891379-65-0, entered Jul. 10, 2006.
STN Registry Database, RN 891379-71-8, entered Jul. 10, 2006.
STN Registry Database, RN 891379-78-5, entered Jul. 10, 2006.
STN Registry Database, RN 891563-66-9, entered Jul. 10, 2006.
STN Registry Database, RN 891569-68-9, entered Jul. 10, 2006.
STN Registry Database, RN 891569-89-4, entered Jul. 10, 2006.
STN Registry Database, RN 891569-97-4, entered Jul. 10, 2006.
STN Registry Database, RN 891590-88-8, entered Jul. 10, 2006.
STN Registry Database, RN 891590-96-8, entered Jul. 10, 2006.
STN Registry Database, RN 891591-04-1, entererd Jul. 10, 2006.
STN Registry Database, RN 891614-21-4, entered Jul. 10, 2006.
STN Registry Database, RN 891631-78-0, entered Jul. 10, 2006.
STN Registry Database, RN 891631-85-9, entered Jul. 10, 2006.
STN Registry Database, RN 894162-80-2, entered Jul. 18, 2006.
STN Registry Database, RN 894305-60-3, entered Jul. 19, 2006.
STN Registry Database, RN 895052-18-3, entered Jul. 23, 2006.
STN Registry Database, RN 903047-29-0, entered Aug. 21, 2006.
STN Registry Database, RN 904139-33-9, entered Aug. 24, 2006.
STN Registry Database, RN 904203-99-2, entered Aug. 24, 2006.
Babu et al., "From Molecular Design to Co-sensitization; High performance indole based photosensitizers for dye-sensitized solar cells," Electrochimica Acta 198 (2016): 10-21.
Yadav et al., "Phosphane-catalyzed Knoevenagel condensation: A facile synthesis of a-cyanoacrylates and a-cyanoacrylonitriles." European Journal of Organic Chemistry (2004): 546-551.
Database Registry Cas, RN 79246-44-9, Entered STN: Nov. 16, 1984.

* cited by examiner

COMPOSITIONS AND METHODS FOR MODULATING HAIR GROWTH

CROSS-REFERENCE TO RELATED APPLICATIONS

This application is the § 371 National Stage of PCT/US2021/039502, filed Jun. 29, 2021, which claims the benefit of U.S. Provisional Patent Application No. 63/046,629, filed Jun. 30, 2020, each of which is incorporated by reference herein in its entirety.

BACKGROUND

Hair follicle stem cells (HFSCs) undergo successive rounds of quiescence (telogen) punctuated by brief periods of proliferation correlating with the start of the hair cycle (telogen-anagen transition). Proliferation or activation of HFSCs is well known to be a prerequisite for advancement of the hair cycle. Despite advances in treatment options, baldness and alopecia continue to be conditions that cannot be successfully treated in many individuals. Some of the existing treatments are inconvenient for users, others require surgical intervention or other invasive procedures. Additional therapies are needed.

SUMMARY

Described herein are compounds of Formula 1:

Formula 1

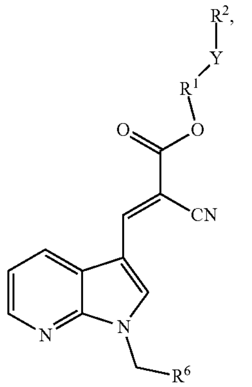

or a pharmaceutically acceptable salt thereof; wherein $R^1$ is -, —S(=O)$_2$—, an optionally substituted $C_{1-12}$ hydrocarbon group or an optionally substituted heterocycle; $R^2$ is H, an optionally substituted $C_{1-6}$ alkyl, an optionally substituted carbocycle, or an optionally substituted heterocycle;

Y is ——, —O—, 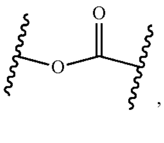 , 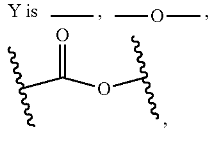 , or

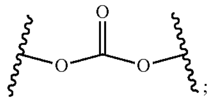 [SMILES: *OC(=O)O*] ;

and $R^6$ is

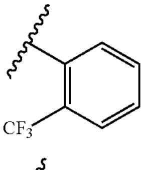 , 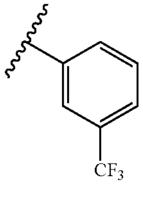 , or 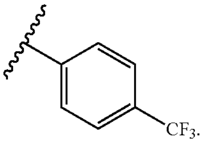 .

In other embodiments, $R^6$ of Formula 1 is

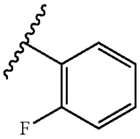 , 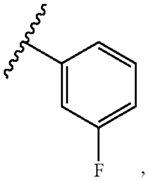 , 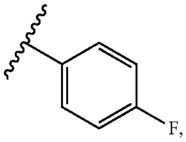 , 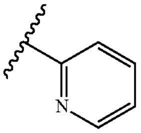 , 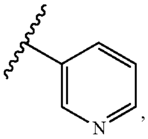 , or 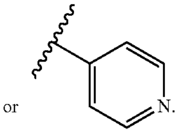 .

Some embodiments include a pharmaceutical composition comprising a compound described herein.

Some embodiments include a method of growing hair, comprising: administering a compound described herein to the skin of a mammal, including a human being, in the area where hair growth is intended.

Some embodiments include a method of growing hair comprising administering an MPO inhibitor to a mammal, including a human being, in need thereof. In some embodiments, the MPO inhibitor is a compound described herein.

Some embodiments include a method of treating a disorder affecting hair growth comprising administering a compound described herein to a mammal, including a human being, in need thereof. In some embodiments, the disorder is alopecia or baldness. Some embodiments include use of a compound described herein in the manufacture of a medicament for growing hair.

Some embodiments include a kit comprising a compound described herein and a label with instructions to administer the compound for a use described herein, such as growing hair.

DETAILED DESCRIPTION

Figure 1:
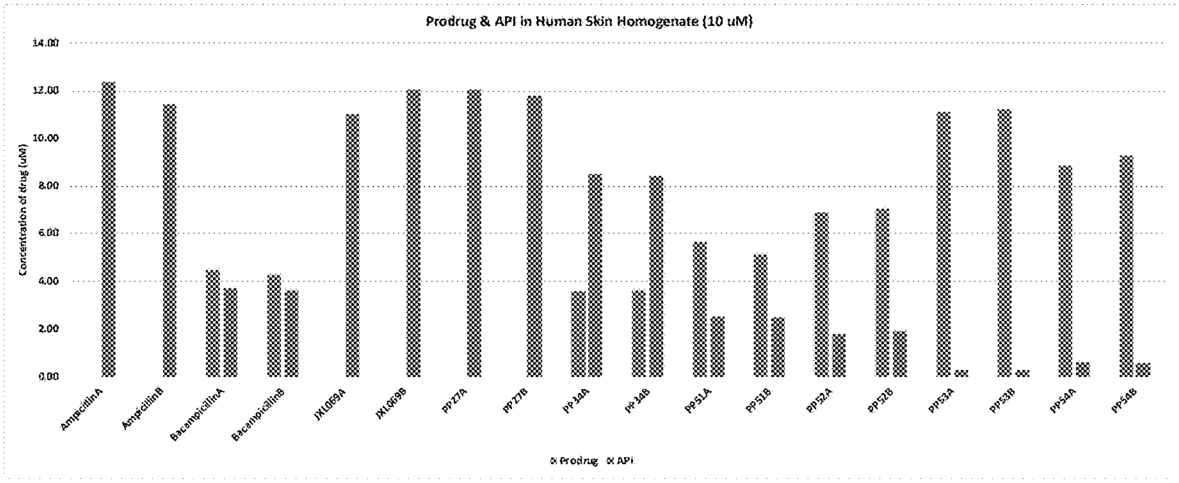
FIG. 1 shows the conversion of ester prodrug (shown in gray) to the corresponding carboxylic acid API (shown in black) after 1 hour of incubation in homogenized human skin at 37° C. and pH 7.4.

Described herein are compounds, compositions, and methods for modulating hair growth. Compounds of the present disclosure include substituted 7-azaindole compounds which may be useful for modulating hair growth.

Unless otherwise indicated, any reference to a compound herein by structure, name, or any other means, includes pharmaceutically acceptable salts, such as sodium, potassium, and ammonium salts; prodrugs, such as ester prodrugs; alternate solid forms, such as polymorphs, solvates, hydrates, etc.; deuterium-modified forms; Z and E olefin isomers; tautomers; or any other chemical species that may rapidly convert to a compound described herein under conditions in which the compounds are used as described herein. In some embodiments, the compound contains more than a natural abundance of deuterium. In some embodiments, one or more of the hydrogen atoms on the compound is replaced by deuterium so that the compound is at least 50%, at least 80%, at least 90%, at least 95%, or at least 99% deuterium in that position.

Unless otherwise indicated, when a compound or chemical structural feature (such as alkyl or aryl) is referred to as being "optionally substituted," it includes a feature that has no substituents (i.e. unsubstituted), or a feature that is "substituted," meaning that the feature has one or more substituents. The term "substituent" has the broadest meaning known to one of ordinary skill in the art, and includes a moiety that occupies a position normally occupied by one or more hydrogen atoms attached to a parent compound or structural feature. In some embodiments, a substituent may be an ordinary organic moiety known in the art, which may have a molecular weight (e.g. the sum of the atomic masses of the atoms of the substituent) of about 15 g/mol to about 50 g/mol, about 15 g/mol to about 100 g/mol, about 15 g/mol to about 150 g/mol, about 15 g/mol to about 200 g/mol, about 15 g/mol to about 300 g/mol, or about 15 g/mol to about 500 g/mol. In some embodiments, a substituent comprises, or consists of: 0-30, 0-20, 0-10, or 0-5 carbon atoms; and 0-30, 0-20, 0-10, or 0-5 heteroatoms, wherein each heteroatom may independently be: N, O, S, P, Si, F, Cl, Br, or I; provided that the substituent includes one C, N, O, S, P, Si, F, Cl, Br, or I atom. Examples of substituents include, but are not limited to, compounds represented by an empirical formula: $C_{1-12}H_{3-29}O_{0-4}N_{0-4}S_{0-4}F_{0-25}Cl_{0-5}Si_{0-3}P_{0-3}$, $C_{0-12}H_{0-29}O_{1-4}N_{0-4}S_{0-4}F_{0-25}Cl_{0-5}Si_{0-3}P_{0-3}$, $C_{0-12}H_{0-29}O_{0-4}N_{1-4}S_{0-4}F_{0-25}Cl_{0-5}Si_{0-3}P_{0-3}$, $C_{0-12}H_{0-29}O_{0-4}N_{0-4}S_{1-4}F_{0-25}Cl_{0-5}Si_{0-3}P_{0-3}$, $C_{0-12}H_{0-29}O_{0-4}N_{0-4}S_{0-4}F_{1-25}Cl_{0-5}Si_{0-3}P_{0-3}$, $C_{0-12}H_{0-29}O_{0-4}N_{0-4}S_{0-4}F_{0-25}Cl_{1-5}Si_{0-3}P_{0-3}$, $C_{0-12}H_{0-29}O_{0-4}N_{0-4}S_{0-4}F_{0-25}Cl_{0-5}Si_{1-3}P_{0-3}$, $C_{0-12}H_{0-29}O_{0-4}N_{0-4}S_{0-4}F_{0-25}Cl_{0-5}Si_{0-3}P_{1-3}$, $C_{1-6}H_{3-16}O_{0-4}N_{0-4}S_{0-4}F_{0-13}Cl_{0-3}Si_{0-3}P_{0-3}$, $C_{0-6}H_{0-16}O_{1-4}N_{0-4}S_{0-4}F_{0-13}Cl_{0-3}Si_{0-3}P_{0-3}$, $C_{0-6}H_{0-17}O_{0-4}N_{1-4}S_{0-4}F_{0-13}Cl_{0-3}Si_{0-3}P_{0-3}$, $C_{0-6}H_{0-17}O_{0-4}N_{0-4}S_{1-4}F_{0-13}Cl_{0-3}Si_{0-3}P_{0-3}$, $C_{0-6}H_{0-17}O_{0-4}N_{0-4}S_{0-4}F_{1-13}Cl_{0-3}Si_{0-3}P_{0-3}$, $C_{0-6}H_{0-17}O_{0-4}N_{0-4}S_{0-4}F_{0-13}Cl_{1-3}Si_{0-3}P_{0-3}$, $C_{0-6}H_{0-17}O_{0-4}N_{0-4}S_{0-4}F_{0-13}Cl_{0-3}Si_{1-3}P_{0-3}$, or $C_{0-6}H_{0-17}O_{0-4}N_{0-4}S_{0-4}F_{0-13}Cl_{0-3}Si_{0-3}P_{1-3}$, $C_{1-12}H_{3-29}O_{0-4}N_{0-4}S_{0-4}F_{0-25}Cl_{0-5}P_{0-3}$, $C_{1-12}H_{3-27}O_{0-4}N_{0-2}S_{0-2}F_{0-25}Cl_{0-5}P_{0-1}$, $C_{1-12}H_{3-27}O_{0-4}N_{0-2}$, $C_{1-12}H_{3-25}O_{0-4}$, $C_{1-12}H_{3-27}N_{0-2}$, $C_{1-9}H_{3-21}O_{0-4}N_{0-2}S_{0-2}F_{0-19}Cl_{0-5}P_{0-1}$, $C_{1-9}H_{3-19}F_{0-19}$, $C_{1-9}H_{3-21}O_{0-4}N_{0-2}$, $C_{1-9}H_{3-19}O_{0-4}$, $C_{1-9}H_{3-21}N_{0-2}$, $C_{1-6}H_{3-15}O_{0-3}N_{0-2}S_{0-2}F_{0-13}Cl_{0-5}P_{0-1}$, $C_{1-6}H_{3-13}F_{0-13}$, $C_{1-6}H_{3-15}O_{0-4}N_{0-2}$, $C_{1-6}H_{3-13}O_{0-4}$, $C_{1-6}H_{3-15}N_{0-2}$, $C_{1-3}H_{3-9}O_{0-3}N_{0-2}S_{0-2}F_{0-13}Cl_{0-5}P_{0-1}$, $C_{1-3}H_{3-7}F_{0-7}$, $C_{1-3}H_{3-9}O_{0-3}N_{0-2}$, $C_{1-3}H_{3-7}O_{0-3}$, $C_{1-3}H_{3-9}N_{0-2}$, F, Cl, Br, I, OH, $OR^A$, SH, $SR^A$, $NH_2$, $NHR^A$, $NR^AR^B$, $CF_3$, CN, carboxylic acid, optionally substituted carboxylic ester, or optionally substituted $C_{1-6}$ alkyl, such as optionally substituted branched $C_{2-6}$ alkyl or optionally substituted linear $C_{1-6}$ alkyl, including optionally substituted branched or linear $C_{1-3}$ alkyl (e.g. $-CH_3$, $-C_2H_5$, $-C_3H_7$), optionally substituted branched, linear, or cyclic $C_{3-6}$ alkyl (e.g. $-C_3H_7$, $-C_4H_9$, $-C_5H_{11}$, $-C_6H_{13}$, cyclopropyl, cyclobutyl, cyclopentyl, cyclohexyl, etc.), alkenyl, alkynyl, heteroalkyl, heteroalkenyl, heteroalkynyl, aryl, heteroaryl, carbocycle, heterocycle, hydroxy, alkoxy, aryloxy, acyl, acyloxy, alkylcarboxylate, thiol, alkylthio, cyano, halo, thiocarbonyl, O-carbamyl, N-carbamyl, O-thiocarbamyl, N-thiocarbamyl, C-amido, N-amido, S-sulfonamido, N-sulfonamido, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, etc.

For convenience, the term "molecular weight" is used with respect to a moiety or part of a molecule to indicate the sum of the atomic masses of the atoms in the moiety or part of a molecule, even though it may not be a complete molecule.

As used herein, the term "alkyl" has the broadest meaning generally understood in the art, and may include a moiety composed of carbon and hydrogen containing no double or triple bonds. Alkyl may be linear alkyl, branched alkyl, cycloalkyl, or a combination thereof, and in some embodiments, may contain from one to thirty-five carbon atoms. In some embodiments, alkyl may include $C_{1-10}$ linear alkyl, such as methyl ($-CH_3$), ethyl ($-CH_2CH_3$), n-propyl ($-CH_2CH_2CH_3$), n-butyl ($-CH_2CH_2CH_2CH_3$), n-pentyl ($-CH_2CH_2CH_2CH_2CH_3$), n-hexyl ($-CH_2CH_2CH_2CH_2CH_2CH_3$), etc.; $C_{3-10}$ branched alkyl, such as $C_{3H7}$ (e.g. iso-propyl), $C_4H_9$ (e.g. branched butyl isomers), $C_5H_{11}$ (e.g. branched pentyl isomers), $C_6H_{13}$ (e.g. branched hexyl isomers), $C_7H_{15}$ (e.g. branched heptyl isomers), etc.; $C_{3-10}$ cycloalkyl, such as $C_3H_5$ (e.g. cyclopropyl), $C_4H_7$ (e.g. cyclobutyl isomers such as cyclobutyl, methylcyclopropyl, etc.), $C_5H_9$ (e.g. cyclopentyl isomers such as cyclopentyl, methylcyclobutyl, dimethylcyclopropyl, etc.), $C_6H_{11}$ (e.g. cyclohexyl isomers), $C_7H_{13}$ (e.g. cycloheptyl isomers), etc.; and the like.

With respect to an optionally substituted moiety such as optionally substituted alkyl, a phrase such as "optionally substituted $C_{1-12}$ alkyl" refers to a $C_{1-12}$ alkyl that may be unsubstituted, or may have 1 or more substituents, and does not limit the number of carbon atoms in any substituent. A phrase such as "$C_{1-12}$ optionally substituted alkyl" refers to unsubstituted $C_{1-12}$ alkyl, or substituted alkyl wherein both the alkyl parent and all substituents have from 1-12 carbon atoms. Similar conventions may be applied to other optionally substituted moieties such as aryl and heteroaryl.

Empirical formulas, such as $C_{1-12}H_{3-25}O_{0-2}N_{0-2}F_{0-12}$, may be used to describe optionally substituted $C_{1-12}$ alkyl chemical compositions. In some embodiments, additional elements S, Si, P, other halogens, or other heteroatoms may also be included in the empirical formula.

The compounds described herein may have any of the following structural representations:

Formula 1

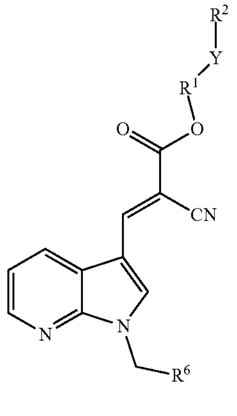

With respect to any relevant structural representation, such as Formula 1, $R^1$ is a bond (represented as -); —S(=O)$_2$—; an optionally substituted $C_{1-12}$ hydrocarbon group, including optionally substituted $C_{1-12}$ alkyl, such as optionally substituted branched $C_{2-12}$ alkyl or optionally substituted linear $C_{1-12}$ alkyl, including optionally substituted branched $C_{2-6}$ alkyl or linear $C_{1-6}$ alkyl, optionally substituted branched $C_{2-3}$ alkyl (e.g., $—CH(CH_3)—$, $—CH(CH_2CH_3)—$, $—C(CH_3)_2—$), or linear $C_{1-3}$ alkyl (e.g., $—CH_2—$, $—C_2H_4—$, $—C_3H_6—$), optionally substituted branched, linear, or cyclic $C_{3-6}$ alkyl (e.g. $—C_3H_6—$, $—C_4H_8—$, $—C_5H_{10}—$, $—C_6H_{12}—$, $—CH(CH_2CH_3)—$, $—CH(CH_3)CH_2—$, $—C(CH_3)_2CH_2—$, $—CH_2CH(CH_3)CH_2—$, $—C(CH_3)(CH_2CH_3)—$, $—CH(CH_2CH_2CH_3)—$, $—C(CH_2CH_3)_2—$, $—C(CH_3)(CH_2CH_2CH_3)—$, $—CH(CH_2CH_2CH_2CH_3)—$, $—C(CH_3)(CH_2CH_2CH_2CH_3)—$, $—CH(CH_2CH_2CH_2CH_2CH_3)—$, $—C(CH_2CH_3)(CH_2CH_2CH_3)$, cyclopropyl, cyclobutyl, cyclopentyl, cyclohexyl, etc.), optionally substituted branched, linear, or cyclic $C_{6-9}$ alkyl (e.g., $—C(CH_3)(CH_2CH_2CH_2CH_3)—$, $—CH(CH_2CH_2CH_2CH_2CH_3)—$, $—C(CH_2CH_3)(CH_2CH_2CH_3)—$, $—C_6H_{12}—$, $—C_7H_{14}—$, $—C_8H_{16}—$, $—C_9H_{18}—$, cyclohexyl, cycloheptyl, cyclooctyl, cyclononyl, etc.), optionally substituted branched, linear, or cyclic $C_{9-12}$ alkyl, $C_{2-12}$ alkenyl, $C_{2-12}$ alkynyl, optionally substituted $C_{3-12}$ carbocycle, optionally substituted benzyl, etc.; optionally substituted carbocycle, including optionally substituted $C_{3-12}$ cycloalkyl, optionally substituted $C_{3-6}$ cycloalkyl, optionally substituted $C_{6-9}$ cycloalkyl, optionally substituted $C_{9-12}$ cycloalkyl, optionally substituted $C_{3-12}$ cycloalkenyl, optionally substituted $C_{3-6}$ cycloalkenyl, optionally substituted $C_{6-9}$ cycloalkenyl, optionally substituted $C_{9-12}$ cycloalkenyl, optionally substituted $C_{3-12}$ cycloalkynyl, optionally substituted $C_{3-6}$ cycloalkynyl, optionally substituted $C_{6-9}$ cycloalkynyl, optionally substituted $C_{9-12}$ cycloalkynyl, optionally substituted phenyl, optionally substituted naphthyl; or optionally substituted heterocycle, such as an optionally substituted monocyclic heterocycle having 3 ring carbon atoms and 1 ring oxygen atom, an optionally substituted monocyclic heterocycle having 4 ring carbon atoms and 1 ring oxygen atom, an optionally substituted monocyclic heterocycle having 5 ring carbon atoms and 1 ring oxygen atom, an optionally substituted monocyclic heterocycle having 6 ring carbon atoms and 1 ring oxygen atom, an optionally substituted monocyclic heterocycle having 7 ring carbon atoms and 1 ring oxygen atom, an optionally substituted monocyclic heterocycle having 3 ring carbon atoms and 1 ring sulfur atom, an optionally substituted monocyclic heterocycle having 4 ring carbon atoms and 1 ring sulfur atom, an optionally substituted monocyclic heterocycle having 5 ring carbon atoms and 1 ring sulfur atom, an optionally substituted monocyclic heterocycle having 6 ring carbon atoms and 1 ring sulfur atom, an optionally substituted monocyclic heterocycle having 7 ring carbon atoms and 1 ring sulfur atom, an optionally substituted monocyclic heterocycle having 3 ring carbon atoms and 1 ring nitrogen atom, an optionally substituted monocyclic heterocycle having 4 ring carbon atoms and 1 ring nitrogen atom, an optionally substituted monocyclic heterocycle having 5 ring carbon atoms and 1 ring nitrogen atom, an optionally substituted monocyclic heterocycle having 6 ring carbon atoms and 1 ring nitrogen atom, an optionally substituted monocyclic heterocycle having 7 ring carbon atoms and 1 ring nitrogen atom, an optionally substituted monocyclic heterocycle having 3 ring carbon atoms and 2 ring heteroatoms (N, O, and/or S), an optionally substituted monocyclic heterocycle having 4 ring carbon atoms and 2 ring heteroatoms (N, O, and/or S), an optionally substituted monocyclic heterocycle having 5 ring carbon atoms and 2 ring heteroatoms (N, O, and/or S), an optionally substituted monocyclic heterocycle having 6 ring carbon atoms and 2 ring heteroatoms (N, O, and/or S), an optionally substituted monocyclic heterocycle having 2 ring carbon atoms and 3 ring heteroatoms (N, O, and/or S), an optionally substituted monocyclic heterocycle having 3 ring carbon atoms and 3 ring heteroatoms (N, O, and/or S), an optionally substituted monocyclic heterocycle having 4 ring carbon atoms and 3 ring heteroatoms (N, O, and/or S), an optionally substituted monocyclic heterocycle having 5 ring carbon atoms and 3 ring heteroatoms (N, O, and/or S), an optionally substituted bicyclic heterocycle having 6 ring carbon atoms and 1 ring heteroatom (N, O, or S), an optionally substituted bicyclic 32 heterocycle having 7 ring carbon atoms and 1 ring heteroatom (N, O, or S), an optionally substituted bicyclic heterocycle having 8 ring carbon atoms and 1 ring heteroatom (N, O, or S), an optionally substituted bicyclic heterocycle having 9 ring carbon atoms and 1 ring heteroatom (N, O, or S), an optionally substituted bicyclic heterocycle having 10 ring carbon atoms and 1 ring heteroatom (N, O, or S), an optionally substituted bicyclic heterocycle having 11 ring carbon atoms and 1 ring heteroatom (N, O, or S), an optionally substituted bicyclic heterocycle having 12 ring carbon atoms and 1 ring heteroatom (N, O, or S), an optionally substituted bicyclic heterocycle having 5 ring carbon atoms and 2 ring heteroatoms (N, O, and/or S), an optionally substituted bicyclic heterocycle having 6 ring carbon atoms and 2 ring heteroatoms (N, O, and/or S), an optionally substituted bicyclic heterocycle having 7 ring carbon atoms and 2 ring heteroatoms (N, O, and/or S), an optionally substituted bicyclic heterocycle having 8 ring carbon atoms and 2 ring heteroatoms (N, O, and/or S), an optionally substituted bicyclic heterocycle having 9 ring carbon atoms and 2 ring heteroatoms (N, O, and/or S), an optionally substituted bicyclic heterocycle having 10 ring carbon atoms and 2 ring heteroatoms (N, O, and/or S), an optionally substituted bicyclic heterocycle having 11 ring carbon atoms and 2 ring heteroatoms (N, O, and/or S), an optionally substituted bicyclic heterocycle having 5 ring carbon atoms and 3 ring heteroatoms (N, O, and/or S), an optionally substituted bicyclic heterocycle having 6 ring carbon atoms and 3 ring heteroatoms (N, O, and/or S), an optionally substituted bicyclic heterocycle having 7 ring carbon atoms and 3 ring heteroatoms (N, O, and/or S), an optionally substituted bicyclic heterocycle having 8 ring carbon atoms and 3 ring heteroatoms (N, O, and/or S), an optionally substituted bicyclic heterocycle having 9 ring carbon atoms and 3 ring heteroatoms (N, O, and/or S), an optionally substituted bicyclic heterocycle having 10 ring carbon atoms and 3 ring heteroatoms (N, O, and/or S), optionally substituted oxetane, optionally substituted tetrahydrofuran, optionally substituted dihydrofuran, optionally substituted furan, optionally substituted furanone, optionally substituted tetrahydropyran, optionally substituted dihydropyran, an optionally substituted pyran, optionally substituted tetrahydropyrone, optionally substituted dihydropyrone, optionally substituted pyrone, optionally substituted thietane, optionally substituted tetrahydrothiophene, optionally substituted dihydrothiophene, an optionally substituted thiophene, optionally substituted azetidine, optionally substituted pyrrolidine, optionally substituted pyrroline, optionally substituted pyrrole, optionally substituted piperidine, optionally substituted pyridine, optionally substituted oxazole, optionally substituted isoxazole, optionally substituted thiazole, optionally substituted isothiazole, optionally substituted pyrazolidine, optionally substituted imidazolidine, optionally substituted pyrazole, optionally substituted imidazole, optionally substituted tetrazole, optionally substituted sulfolane.

For the purposes of this disclosure, the term "alkyl" refers to both monovalent groups (such as $—CH_3$), bivalent groups (such as $—CH_2—$), or other hydrocarbon groups with higher valency that are free of double and triple bonds.

In some embodiments, $R^1$ is -. In some embodiments, $R^1$ is $C_{1-12}$ alkyl. In some embodiments, $R^1$ is linear $C_{1-12}$ alkyl. In some embodiments, $R^1$ is branched $C_{2-12}$ alkyl. In some embodiments, $R^1$ is $—CH_2—$, $—C_2H_4—$, $—C_3H_6—$, $—C_3H_6—$, $—C_4H_8—$, $—C_5H_{10}—$, $—C_6H_{12}—$, $—C_7H_{14}—$, $—C_8H_{16}—$, or $—C_9H_{18}—$. In some embodiments, $R^1$ is $—CH_2—$. In some embodiments, $R^1$ is $—C_2H_4—$. In some embodiments, $R^1$ is $—C_3H_6—$. In some embodiments, $R^1$ is $—C_3H_6—$.

In some embodiments, $R^1$ is $—C_4H_8—$. In some embodiments, $R^1$ is $—C_5H_{10}—$. In some embodiments, $R^1$ is $—C_6H_{12}—$. In some embodiments, $R^1$ is $—C_7H_{14}—$. In some embodiments, $R^1$ is $—C_8H_{16}—$. In some embodiments, $R^1$ is $—C_9H_{18}—$. In some embodiments, $R^1$ is an optionally substituted linear $C_{1-12}$ alkyl. In some embodiments, $R^1$ is an optionally substituted branched $C_{2-12}$ alkyl. In some embodiments, $R^1$ is an optionally heteroatom substituted branched $C_{2-12}$ alkyl, such as a branched $C_{2-12}$ alkyl having polar substituents, including oxygen containing groups (e.g. —OH, =O, $OCH_3$, etc.), sulfur containing groups (e.g. —SH, $—SCH_3$, $SO_2$, $SO_3^-$, etc.), nitrogen containing groups (e.g. amino groups such as $—NH_2$, $—NHCH_3$, $—N(CH_3)_2$, quaternary ammonium salts such as $—[N(CH_3)_2]^+$, $—[N(CH_2CH_3)(CH_3)]^+$, $—NO_2$, —CN, etc.), fluorine containing groups (e.g. F, $CF_3$, $CF_2CF_3$, $CHF_2$, $CH_2F$, $CF_2CF_2CF_3$, etc.).

In some embodiments, $R^1$ is an optionally substituted carbocycle. In some embodiments, $R^1$ is optionally substituted cyclohexyl. In some embodiments, $R^1$ is an optionally substituted aryl. In some embodiments, $R^1$ is an optionally substituted phenyl. In some embodiments, $R^1$ is an optionally substituted benzyl. In some embodiments, $R^1$ is an optionally substituted heteroaryl. In some embodiments, $R^1$ is an optionally substituted heterocycle. In some embodiments wherein $R^1$ is an optionally substituted heterocycle, a carbon atom of the heterocycle (rather than a heteroatom of the heterocycle) is directly attached to O. In some embodiments wherein $R^1$ is an optionally substituted heterocycle, a carbon atom of the heterocycle ring (rather than a heteroatom of the heterocycle ring) is directly attached to Y. In some embodiments, $R^1$ is an optionally heteroatom substituted carbocycle, such as a carbocycle having polar substituents, including oxygen containing groups (e.g. —OH, =O, $OCH_3$, etc.), sulfur containing groups (e.g. —SH, $—SCH_3$, $SO_2$, $SO_3^-$, etc.), nitrogen containing groups (e.g. amino groups such as $—NH_2$, $—NHCH_3$, $—N(CH_3)_2$, quaternary ammonium salts such as $—[N(CH_3)_2]^+$, $—[N(CH_2CH_3)(CH_3)]^+$, $—NO_2$, —CN, etc.), fluorine containing groups (e.g. F, $CF_3$, $CF_2CF_3$, $CHF_2$, $CH_2F$, $CF_2CF_2CF_3$, etc.). In some embodiments, $R^1$ is an optionally heteroatom substituted heterocycle, such as a heterocycle having polar substituents, including oxygen containing groups (e.g. —OH, =O, $OCH_3$, etc.), sulfur containing groups (e.g. —SH, $—SCH_3$, $SO_2$, $SO_3^-$, etc.), nitrogen containing groups (e.g. $—NH_2$, $—NHCH_3$, $—N(CH_3)_2$, $—NO_2$, —CN, etc.), fluorine containing groups (F, $CF_3$, $CF_2CF_3$, $CHF_2$, $CH_2F$, $CF_2CF_2CF_3$, etc.). In some embodiments, $R^1$ is an optionally heteroatom substituted benzyl, such as a benzyl having polar substituents, including oxygen containing groups (e.g. —OH, =O, $OCH_3$, etc.), sulfur containing groups (e.g. —SH, $—SCH_3$, $SO_2$, $SO_3^-$, etc.), nitrogen containing groups (e.g. $—NH_2$, $—NHCH_3$, $—N(CH_3)_2$, $—NO_2$, —CN, etc.), fluorine containing groups (e.g. F, $CF_3$, $CF_2CF_3$, $CHF_2$, $CH_2F$, $CF_2CF_2CF_3$, etc.).

In some embodiments, $R^1$ is an optionally substituted oxetane. In some embodiments, $R^1$ is an optionally substituted oxetane having a carbon atom of the oxetane ring directly attached to the O atom.

In some embodiments, $R^1$ is an optionally substituted tetrahydrofuran. In some embodiments, $R^1$ is an optionally substituted tetrahydrofuran having a carbon atom of the tetrahydrofuran ring directly attached to the O atom.

In some embodiments, $R^1$ is an optionally substituted dihydrofuran. In some embodiments, $R^1$ is an optionally substituted dihydrofuran having a carbon atom of the dihydrofuran ring directly attached to the O atom.

In some embodiments, $R^1$ is an optionally substituted furan. In some embodiments, $R^1$ is an optionally substituted furan having a carbon atom of the furan ring directly attached to the O atom.

In some embodiments, $R^1$ is an optionally substituted furanone. In some embodiments, $R^1$ is an optionally substituted furanone having a carbon atom of the furanone ring directly attached to the O atom.

In some embodiments, $R^1$ is an optionally substituted tetrahydropyran. In some embodiments, $R^1$ is an optionally substituted tetrahydropyran having a carbon atom of the tetrahydropyran ring directly attached to the O atom.

In some embodiments, $R^1$ is an optionally substituted dihydropyran. In some embodiments, $R^1$ is an optionally substituted dihydropyran having a carbon atom of the dihydropyran ring directly attached to the O atom.

In some embodiments, $R^1$ is an optionally substituted pyran. In some embodiments, $R^1$ is an optionally substituted pyran having a carbon atom of the pyran ring directly attached to the O atom.

In some embodiments, $R^1$ is an optionally substituted tetrahydropyrone. In some embodiments, $R^1$ is an optionally substituted tetrahydropyrone having a carbon atom of the tetrahydropyrone ring directly attached to the O atom.

In some embodiments, $R^1$ is an optionally substituted dihydropyrone. In some embodiments, $R^1$ is an optionally substituted dihydropyrone having a carbon atom of the dihydropyrone ring directly attached to the O atom.

In some embodiments, $R^1$ is an optionally substituted pyrone. In some embodiments, $R^1$ is an optionally substituted pyrone having a carbon atom of the pyrone ring directly attached to the O atom.

In some embodiments, $R^1$ is an optionally substituted thietane. In some embodiments, $R^1$ is an optionally substituted thietane having a carbon atom of the thietane ring directly attached to the O atom.

In some embodiments, $R^1$ is an optionally substituted tetrahydrothiophene. In some embodiments, $R^1$ is an optionally substituted tetrahydrothiophene having a carbon atom of the tetrahydrothiophene ring directly attached to the O atom.

In some embodiments, $R^1$ is an optionally substituted dihydrothiophene. In some embodiments, $R^1$ is an optionally substituted dihydrothiophene having a carbon atom of the dihydrothiophene ring directly attached to the O atom.

In some embodiments, $R^1$ is an optionally substituted thiophene. In some embodiments, $R^1$ is an optionally substituted thiophene having a carbon atom of the thiophene ring directly attached to the O atom.

In some embodiments, $R^1$ is an optionally substituted azetidine. In some embodiments, $R^1$ is an optionally substituted azetidine having a carbon atom of the azetidine ring directly attached to the O atom. In some embodiments, $R^1$ is azetidine having an optionally substituted diphenylmethyl substituent. In some embodiments, $R^1$ is azetidine having an optionally substituted diphenylmethyl substituent attached to the nitrogen atom of the azetidine ring.

In some embodiments, $R^1$ is an optionally substituted pyrrolidine. In some embodiments, $R^1$ is an optionally substituted pyrrolidine having a carbon atom of the pyrrolidine ring directly attached to the O atom.

In some embodiments, $R^1$ is an optionally substituted pyrroline. In some embodiments, $R^1$ is an optionally substituted pyrroline having a carbon atom of the pyrroline ring directly attached to the O atom.

In some embodiments, $R^1$ is an optionally substituted pyrrole. In some embodiments, $R^1$ is an optionally substituted pyrrole having a carbon atom of the pyrrole ring directly attached to the O atom.

In some embodiments, $R^1$ is an optionally substituted piperidine. In some embodiments, $R^1$ is an optionally substituted piperidine having a carbon atom of the piperidine ring directly attached to the O atom.

In some embodiments, $R^1$ is an optionally substituted pyridine. In some embodiments, $R^1$ is an optionally substituted pyridine having a carbon atom of the pyridine ring directly attached to the O atom.

In some embodiments, $R^1$ is an optionally substituted oxazole. In some embodiments, $R^1$ is an optionally substituted oxazole having a carbon atom of the oxazole ring directly attached to the O atom.

In some embodiments, $R^1$ is an optionally substituted isoxazole. In some embodiments, $R^1$ is an optionally substituted isoxazole having a carbon atom of the isoxazole ring directly attached to the O atom.

In some embodiments, $R^1$ is an optionally substituted thiazole. In some embodiments, $R^1$ is an optionally substituted thiazole having a carbon atom of the thiazole ring directly attached to the O atom.

In some embodiments, $R^1$ is an optionally substituted isothiazole. In some embodiments, $R^1$ is an optionally substituted isothiazole having a carbon atom of the isothiazole ring directly attached to the O atom.

In some embodiments, $R^1$ is an optionally substituted pyrazolidine. In some embodiments, $R^1$ is an optionally substituted pyrazolidine having a carbon atom of the pyrazolidine ring directly attached to the O atom.

In some embodiments, $R^1$ is an optionally substituted imidazolidine. In some embodiments, $R^1$ is an optionally substituted imidazolidine having a carbon atom of the imidazolidine ring directly attached to the O atom.

In some embodiments, $R^1$ is an optionally substituted pyrazole. In some embodiments, $R^1$ is an optionally substituted pyrazole having a carbon atom of the pyrazole ring directly attached to the O atom.

In some embodiments, $R^1$ is an optionally substituted imidazole. In some embodiments, $R^1$ is an optionally substituted imidazole having a carbon atom of the imidazole ring directly attached to the O atom.

In some embodiments, $R^1$ is an optionally substituted tetrazole. In some embodiments, $R^1$ is an optionally substituted tetrazole having a carbon atom of the tetrazole ring directly attached to the O atom.

In some embodiments, $R^1$ is an optionally substituted sulfolane. In some embodiments, $R^1$ is an optionally substituted sulfolane having a carbon atom of the sulfolane ring directly attached to the O atom.

In some embodiments, $R^1$ is $—S(=O)_2—$.

In some embodiments, $R^1$ is $—CH_2—$, $—CH_2CH(CH_3)CH_2—$, or oxetane having a carbon atom of the oxetane ring directly attached to the O atom. In some embodiments, $R^1$ is $—CH_2—$. In some embodiments, $R^1$ is $—CH_2CH(CH_3)CH_2—$. In some embodiments, $R^1$ is oxetane having a carbon atom of the oxetane ring directly attached to the O atom.

In some embodiments, for a compound of Formula 1, $R^1$ is -, $—CH_2—$, an optionally substituted $C_{3-12}$ hydrocarbon group, or an optionally substituted heterocycle having a carbon atom directly attached to the O atom.

With respect to any relevant structural representation, such as Formula 1, $R^2$ is H; optionally substituted $C_{1-12}$ alkyl, optionally substituted $C_{1-6}$ alkyl group, such as optionally substituted branched $C_{3-6}$ alkyl or linear $C_{1-6}$ alkyl, optionally substituted branched $C_3$ alkyl (e.g., $—CH(CH_3)_2$), or optionally substituted linear $C_{1-3}$ alkyl (e.g., $—CH_3$, $—C_2H_5$, $—C_3H_7$), optionally substituted branched, linear, or cyclic $C_{3-6}$ alkyl (e.g. $—C_3H_7$, $—C_4H_9$, $—C_5H_{11}$, $—C_6H_{13}$, $—CH(CH_3)_2$, $—CH(CH_3)(CH_2CH_3)$, $—C(CH_3)_3$, $—CH(CH_2CH_3)_2$, $—CH(CH_3)(CH_2CH_2CH_3)$, $—C(CH_3)_2(CH_2CH_3)$, $—CH_2CH_2CH_2CH(CH_3)_2$, $—CH_2CH(CH_3)CH_2CH_2CH_3$, $—CH_2CH_2CH(CH_3)CH_2CH_3$, $—CH(CH_2CH_3)(CH_2CH_2CH_3)$, $—C(CH_3)(CH_2CH_3)_2$, cyclopropyl, cyclobutyl, cyclopentyl, cyclohexyl, etc.); optionally substituted carbocycle, including optionally substituted $C_{3-6}$ cycloalkyl, optionally substituted $C_{3-6}$ cycloalkenyl, optionally substituted $C_{3-6}$ cycloalkynyl, optionally substituted phenyl; or optionally substituted heterocycle such as an optionally substituted monocyclic heterocycle having 3 ring carbon atoms and 1 ring oxygen atom, an optionally substituted monocyclic heterocycle having 4 ring carbon atoms and 1 ring oxygen atom, an optionally substituted monocyclic heterocycle having 5 ring carbon atoms and 1 ring oxygen atom, an optionally substituted monocyclic heterocycle having 6 ring carbon atoms and 1 ring oxygen atom, an optionally substituted monocyclic heterocycle having 7 ring carbon atoms and 1 ring oxygen atom, an optionally substituted monocyclic heterocycle having 3 ring carbon atoms and 1 ring sulfur atom, an optionally substituted monocyclic heterocycle having 4 ring carbon atoms and 1 ring sulfur atom, an optionally substituted monocyclic heterocycle having 5 ring carbon atoms and 1 ring sulfur atom, an optionally substituted monocyclic heterocycle having 6 ring carbon atoms and 1 ring sulfur atom, an optionally substituted monocyclic heterocycle having 7 ring carbon atoms and 1 ring sulfur atom, an optionally substituted monocyclic heterocycle having 3 ring carbon atoms and 1 ring nitrogen atom, an optionally substituted monocyclic heterocycle having 4 ring carbon atoms and 1 ring nitrogen atom, an optionally substituted monocyclic heterocycle having 5 ring carbon atoms and 1 ring nitrogen atom, an optionally substituted monocyclic heterocycle having 6 ring carbon atoms and 1 ring nitrogen atom, an optionally substituted monocyclic heterocycle having 7 ring carbon atoms and 1 ring nitrogen atom, an optionally substituted monocyclic heterocycle having 3 ring carbon atoms and 2 ring heteroatoms (N, O, and/or S), an optionally substituted monocyclic heterocycle having 4 ring carbon atoms and 2 ring heteroatoms (N, O, and/or S), an optionally substituted monocyclic heterocycle having 5 ring carbon atoms and 2 ring heteroatoms (N, O, and/or S), an optionally substituted monocyclic heterocycle having 6 ring carbon atoms and 2 ring heteroatoms (N, O, and/or S), an optionally substituted monocyclic heterocycle having 2 ring carbon atoms and 3 ring heteroatoms (N, O, and/or S), an optionally substituted monocyclic heterocycle having 3 ring carbon atoms and 3 ring heteroatoms (N, O, and/or S), an optionally substituted monocyclic heterocycle having 4 ring carbon atoms and 3 ring heteroatoms (N, O, and/or S), an optionally substituted monocyclic heterocycle having 5 ring carbon atoms and 3 ring heteroatoms (N, O, and/or S), an optionally substituted bicyclic heterocycle having 6 ring carbon atoms and 1 ring heteroatom (N, O, or S), an optionally substituted bicyclic heterocycle having 7 ring carbon atoms and 1 ring heteroatom (N, O, or S), an optionally substituted bicyclic heterocycle having 8 ring carbon atoms and 1 ring heteroatom (N, O, or S), an optionally substituted bicyclic heterocycle having 9 ring carbon atoms and 1 ring heteroatom (N, O, or S), an optionally substituted bicyclic heterocycle having 10 ring carbon atoms and 1 ring heteroatom (N, O, or S), an optionally substituted bicyclic heterocycle having 11 ring carbon atoms and 1 ring heteroatom (N, O, or S), an optionally substituted bicyclic heterocycle having 12 ring carbon atoms and 1 ring heteroatom (N, O, or S), an optionally substituted bicyclic heterocycle having 5 ring carbon atoms and 2 ring heteroatoms (N, O, and/or S), an optionally substituted bicyclic heterocycle having 6 ring carbon atoms and 2 ring heteroatoms (N, O, and/or S), an optionally substituted bicyclic heterocycle having 7 ring carbon atoms and 2 ring heteroatoms (N, O, and/or S), an optionally substituted bicyclic heterocycle having 8 ring carbon atoms and 2 ring heteroatoms (N, O, and/or S), an optionally substituted bicyclic heterocycle having 9 ring carbon atoms and 2 ring heteroatoms (N, O, and/or S), an optionally substituted bicyclic heterocycle having 10 ring carbon atoms and 2 ring heteroatoms (N, O, and/or S), an optionally substituted bicyclic heterocycle having 11 ring carbon atoms and 2 ring heteroatoms (N, O, and/or S), an optionally substituted bicyclic heterocycle having 5 ring carbon atoms and 3 ring heteroatoms (N, O, and/or S), an optionally substituted bicyclic heterocycle having 6 ring carbon atoms and 3 ring heteroatoms (N, O, and/or S), an optionally substituted bicyclic heterocycle having 7 ring carbon atoms and 3 ring heteroatoms (N, O, and/or S), an optionally substituted bicyclic heterocycle having 8 ring carbon atoms and 3 ring heteroatoms (N, O, and/or S), an optionally substituted bicyclic heterocycle having 9 ring carbon atoms and 3 ring heteroatoms (N, O, and/or S), an optionally substituted bicyclic heterocycle having 10 ring carbon atoms and 3 ring heteroatoms (N, O, and/or S), optionally substituted oxetane, optionally substituted tetrahydrofuran, optionally substituted dihydrofuran, optionally substituted furan, optionally substituted furanone, optionally substituted tetrahydropyran, optionally substituted dihydropyran, an optionally substituted pyran, optionally substituted tetrahydropyrone, optionally substituted dihydropyrone, optionally substituted pyrone, optionally substituted thietane, optionally substituted tetrahydrothiophene, optionally substituted dihydrothiophene, an optionally substituted thiophene, optionally substituted azetidine, optionally substituted pyrrolidine, optionally substituted pyrroline, optionally substituted pyrrole, optionally substituted piperidine, optionally substituted pyridine, optionally substituted oxazole, optionally substituted isoxazole, optionally substituted thiazole, optionally substituted isothiazole, optionally substituted pyrazolidine, optionally substituted imidazolidine, optionally substituted pyrazole, optionally substituted imidazole, optionally substituted tetrazole, optionally substituted sulfolane.

In some embodiments, $R^2$ is H. In some embodiments, $R^2$ is $C_{1-6}$ alkyl. In some embodiments, $R^2$ is branched $C_{2-6}$ alkyl. In some embodiments, $R^2$ is $—CH_3$, $—C_2H_5$, $—C_3H_7$, $C_4H_9$, $—C_5H_{11}$, or $—C_6H_{13}$. In some embodiments, $R^2$ is $—CH_3$. In some embodiments, $R^2$ is $—C_2H_5$. In some embodiments, $R^2$ is $—C_3H_7$. In some embodiments, $R^2$ is $—C_4H_9$. In some embodiments, $R^2$ is $—C_5H_{11}$. In some embodiments, $R^2$ is $—C_6H_{13}$. In some embodiments, $R^2$ is an optionally substituted linear $C_{1-6}$ alkyl. In some embodiments, $R^2$ is isopropyl. In some embodiments, $R^2$ is isobutyl. In some embodiments, $R^2$ is tert-butyl. In some embodiments, $R^2$ is fluoro substituted $C_{1-6}$ alkyl, including $C_{1-6}$ perfluoralkyl. In some embodiments, $R^2$ is fluoro substituted branched $C_{2-6}$ alkyl, such as branched $C_{2-6}$ perfluoroalkyl. In some embodiments, $R^2$ is $—CF_3$, $—C_2F_5$, $—C_3F_7$, $—C_4F_9$, $—C_5F_{11}$, or $—C_6F_{13}$. In some embodiments, $R^2$ is $—CF_3$. In some embodiments, $R^2$ is $—C_2F_5$. In some embodiments, $R^2$ is $—C_3F_7$. In some embodiments, $R^2$ is $—C_4F_9$. In some embodiments, $R^2$ is $—C_5F_{11}$. In some embodiments, $R^2$ is $—C_6F_{13}$. In some embodiments, $R^2$ is $CF_3$. In some embodiments, $R^2$ is $CHF_2$. In some embodiments, $R^2$ is $CH_2F$. In some embodiments, $R^2$ is $CF_2CF_3$. In some embodiments, $R^2$ is $CF_2CF_2CF_3$. In some embodiments, $R^2$ is fluoro substituted isopropyl, including perfluoroisopropyl. In some embodiments, $R^2$ is fluoro substituted isobutyl, including perfluoroisobutyl. In some embodiments, $R^2$ is fluoro substituted tert-butyl including perfluoro-tert-butyl.

In some embodiments, $R^2$ is an optionally substituted carbocycle. In some embodiments, $R^2$ is optionally substituted cyclohexyl. In some embodiments, $R^2$ is an optionally substituted aryl. In some embodiments, $R^2$ is an optionally substituted phenyl. In some embodiments, $R^2$ is optionally substituted benzyl. In some embodiments, $R^2$ is an optionally substituted heteroaryl. In some embodiments, $R^2$ is an optionally substituted heterocycle. In some embodiments wherein $R^2$ is an optionally substituted heterocycle, a carbon atom of the heterocycle (rather than a heteroatom of the heterocycle) is directly attached to Y.

In some embodiments, $R^2$ is an optionally substituted carbocycle, such as a carbocycle having electron-withdrawing substituents including acyl groups (e.g., —C(O)R, etc.) esters (e.g., $—CO_2R$, etc.), amides (e.g., $—C(O)NR_2$, etc.), imides (e.g., —C(O)NRC(O)R, etc.), cyano (—CN), sulfones (e.g., $—SO_2R$, etc.), sulfonamides (e.g., $—SO_2NR_2$), fluorine or fluorine containing groups (e.g., F, $CF_3$, $CF_2CF_3$, $CHF_2$, $CH_2F$, $CF_2CF_2CF_3$, etc.), and/or nitro ($—NO_2$). In some aspects, $R^2$ is an electron-deficient heterocyclic moiety.

In some embodiments, $R^2$ is an optionally substituted oxetane. In some embodiments, $R^2$ is an optionally substituted oxetane having a carbon atom of the oxetane ring directly attached to Y.

In some embodiments, $R^2$ is an optionally substituted tetrahydrofuran. In some embodiments, $R^2$ is an optionally substituted tetrahydrofuran having a carbon atom of the tetrahydrofuran ring directly attached to Y.

In some embodiments, $R^2$ is an optionally substituted dihydrofuran. In some embodiments, $R^2$ is an optionally substituted dihydrofuran having a carbon atom of the dihydrofuran ring directly attached to Y.

In some embodiments, $R^2$ is an optionally substituted furan. In some embodiments, $R^2$ is an optionally substituted furan having a carbon atom of the furan ring directly attached to Y.

In some embodiments, $R^2$ is an optionally substituted furanone. In some embodiments, $R^2$ is an optionally substituted furanone having a carbon atom of the furanone ring directly attached to Y.

In some embodiments, $R^2$ is an optionally substituted tetrahydropyran. In some embodiments, $R^2$ is an optionally substituted tetrahydropyran having a carbon atom of the tetrahydropyran ring directly attached to Y.

In some embodiments, $R^2$ is an optionally substituted dihydropyran. In some embodiments, $R^2$ is an optionally substituted dihydropyran having a carbon atom of the dihydropyran ring directly attached to Y.

In some embodiments, $R^2$ is an optionally substituted pyran. In some embodiments, $R^2$ is an optionally substituted pyran having a carbon atom of the pyran ring directly attached to Y.

In some embodiments, $R^2$ is an optionally substituted tetrahydropyrone. In some embodiments, $R^2$ is an optionally substituted tetrahydropyrone having a carbon atom of the tetrahydropyrone ring directly attached to Y.

In some embodiments, $R^2$ is an optionally substituted dihydropyrone. In some embodiments, $R^2$ is an optionally substituted dihydropyrone having a carbon atom of the dihydropyrone ring directly attached to Y.

In some embodiments, $R^2$ is an optionally substituted pyrone. In some embodiments, $R^2$ is an optionally substituted pyrone having a carbon atom of the pyrone ring directly attached to Y.

In some embodiments, $R^2$ is an optionally substituted thietane. In some embodiments, $R^2$ is an optionally substituted thietane having a carbon atom of the thietane ring directly attached to Y.

In some embodiments, $R^2$ is an optionally substituted tetrahydrothiophene. In some embodiments, $R^2$ is an optionally substituted tetrahydrothiophene having a carbon atom of the tetrahydrothiophene ring directly attached to Y.

In some embodiments, $R^2$ is an optionally substituted dihydrothiophene. In some embodiments, $R^2$ is an optionally substituted dihydrothiophene having a carbon atom of the dihydrothiophene ring directly attached to Y.

In some embodiments, $R^2$ is an optionally substituted thiophene. In some embodiments, $R^2$ is an optionally substituted thiophene having a carbon atom of the thiophene ring directly attached to Y.

In some embodiments, $R^2$ is an optionally substituted azetidine. In some embodiments, $R^2$ is an optionally substituted azetidine having a carbon atom of the azetidine ring directly attached to Y. In some embodiments, $R^2$ is azetidine having an optionally substituted diphenylmethyl substituent. In some embodiments, $R^2$ is azetidine having an optionally substituted diphenylmethyl substituent attached to the nitrogen atom of the azetidine ring.

In some embodiments, $R^2$ is an optionally substituted pyrrolidine. In some embodiments, $R^2$ is an optionally substituted pyrrolidine having a carbon atom of the pyrrolidine ring directly attached to Y.

In some embodiments, $R^2$ is an optionally substituted pyrroline. In some embodiments, $R^2$ is an optionally substituted pyrroline having a carbon atom of the pyrroline ring directly attached to Y.

In some embodiments, $R^2$ is an optionally substituted pyrrole. In some embodiments, $R^2$ is an optionally substituted pyrrole having a carbon atom of the pyrrole ring directly attached to Y.

In some embodiments, $R^2$ is an optionally substituted piperidine. In some embodiments, $R^2$ is an optionally substituted piperidine having a carbon atom of the piperidine ring directly attached to Y.

In some embodiments, $R^2$ is an optionally substituted pyridine. In some embodiments, $R^2$ is an optionally substituted pyridine having a carbon atom of the pyridine ring directly attached to Y.

In some embodiments, $R^2$ is an optionally substituted oxazole. In some embodiments, $R^2$ is an optionally substituted oxazole having a carbon atom of the oxazole ring directly attached to Y.

In some embodiments, $R^2$ is an optionally substituted isoxazole. In some embodiments, $R^2$ is an optionally substituted isoxazole having a carbon atom of the isoxazole ring directly attached to Y.

In some embodiments, $R^2$ is an optionally substituted thiazole. In some embodiments, $R^2$ is an optionally substituted thiazole having a carbon atom of the thiazole ring directly attached to Y.

In some embodiments, $R^2$ is an optionally substituted isothiazole. In some embodiments, $R^2$ is an optionally substituted isothiazole having a carbon atom of the isothiazole ring directly attached to Y.

In some embodiments, $R^2$ is an optionally substituted pyrazolidine. In some embodiments, $R^2$ is an optionally substituted pyrazolidine having a carbon atom of the pyrazolidine ring directly attached to Y.

In some embodiments, $R^2$ is an optionally substituted imidazolidine. In some embodiments, $R^2$ is an optionally substituted imidazolidine having a carbon atom of the imidazolidine ring directly attached to Y.

In some embodiments, $R^2$ is an optionally substituted pyrazole. In some embodiments, $R^2$ is an optionally substituted pyrazole having a carbon atom of the pyrazole ring directly attached to Y.

In some embodiments, $R^2$ is an optionally substituted imidazole. In some embodiments, $R^2$ is an optionally substituted imidazole having a carbon atom of the imidazole ring directly attached to Y.

In some embodiments, $R^2$ is an optionally substituted tetrazole. In some embodiments, $R^2$ is an optionally substituted tetrazole having a carbon atom of the tetrazole ring directly attached to Y.

In some embodiments, $R^2$ is an optionally substituted sulfolane. In some embodiments, $R^2$ is an optionally substituted sulfolane having a carbon atom of the sulfolane ring directly attached to Y.

In some more particular but non-limiting forms, $R^2$ is H, $-CH_3$, $-CH_2CH_3$, $-CH(CH_3)_2$, or $-C(CH_3)_3$. In some embodiments, $R^2$ is $-CH_2CH_3$. In some embodiments, $R^2$ is $-CH(CH_3)_2$.

With respect to any relevant structural representation, such as Formula 1, in some embodiments, $R^2$ is $CH_3$ or $C_{3-12}$ alkyl, such as branched $C_3$ alkyl (e.g., $—CH(CH_3)_2$), or linear $C_{1-3}$ alkyl (e.g., $—CH_3$, $—C_2H_5$, $—C_3H_7$), branched, linear, or cyclic $C_{3-6}$ alkyl (e.g. $—C_3H_7$, $—C_4H_9$, $—C_5H_{11}$, $—C_6H_{13}$, $—CH(CH_3)_2$, $—CH(CH_3)(CH_2CH_3)$, $—C(CH_3)_3$, $—CH(CH_2CH_3)_2$, $—CH(CH_3)(CH_2CH_2CH_3)$, $—C(CH_3)_2(CH_2CH_3)$, $—CH_2CH_2CH_2CH(CH_3)_2$, $—CH_2CH(CH_3)CH_2CH_2CH_3$, $—CH_2CH_2CH(CH_3)CH_2CH_3$, $—CH(CH_2CH_3)(CH_2CH_2CH_3)$, $—C(CH_3)(CH_2CH_3)_2$, cyclopropyl, cyclobutyl, cyclopentyl, cyclohexyl, etc.).

With respect to any relevant structural representation, such as Formula 1, Y is -, —

O—, 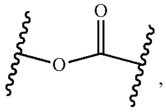, 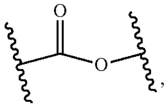, or

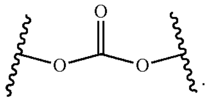

In some embodiments, Y is -. In some embodiments, Y is —O—. In some embodiments, Y is

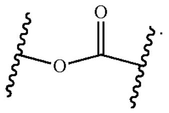 [SMILES: *OC(*)=O]

In some embodiments, Y is

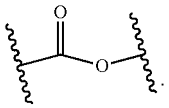 [SMILES: *OC(*)=O]

In some embodiments, Y is

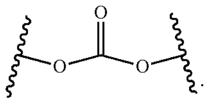 [SMILES: *OC(=O)O*]

In some embodiments, Y is - or

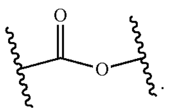 [SMILES: *OC(*)=O]

With respect to any relevant structural representation, such as Formula 1, $R^6$ is

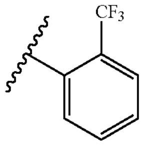, 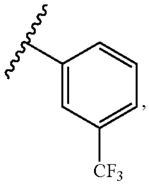, or

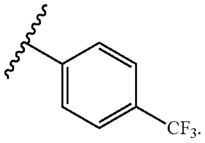

In other embodiments, $R^6$ is

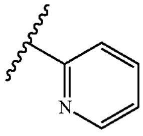, 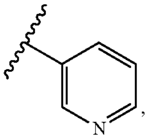, 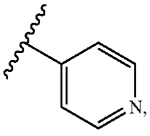

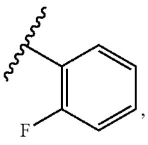, 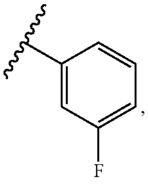, or 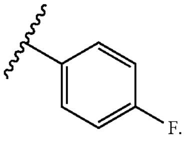

In some embodiments, $R^6$ is

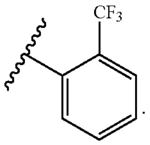 [SMILES: *c1ccccc1C(F)(F)F]

In some embodiments, $R^6$ is

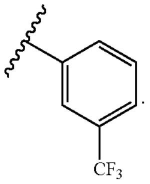

In some embodiments, $R^6$ is

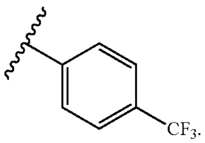 [SMILES: *c1ccc(C(F)(F)F)cc1]

is
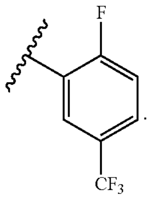 [SMILES: *c1cc(C(F)(F)F)ccc1F]
In some embodiments, $R^6$ is
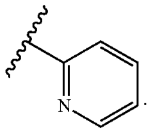
In some embodiments, $R^6$ is
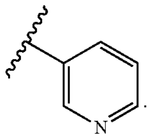 [SMILES: *c1cccnc1]
In some embodiments, $R^6$ is
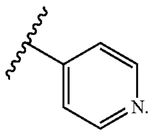 [SMILES: *c1ccncc1]
In some embodiments, $R^6$ is
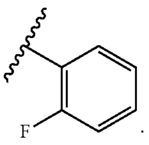 [SMILES: *c1ccccc1F]
In some embodiments, $R^6$ is
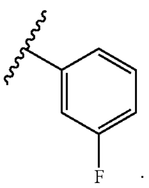 [SMILES: *c1cccc(F)c1]
In some embodiments, $R^6$ is
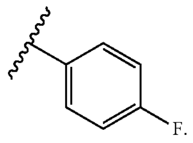 [SMILES: *c1ccc(F)cc1]
In some embodiments, the compound is a compound shown below, each of which may be optionally substituted:
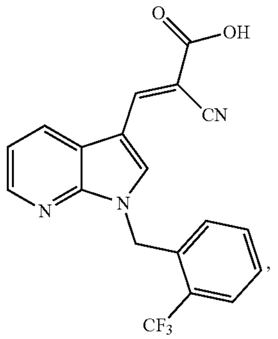
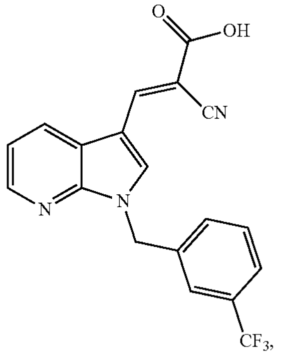
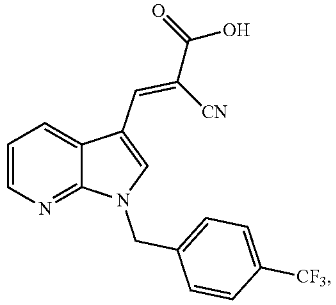
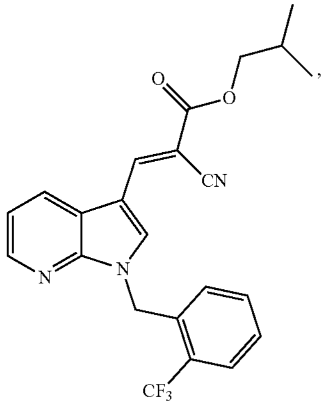

-continued
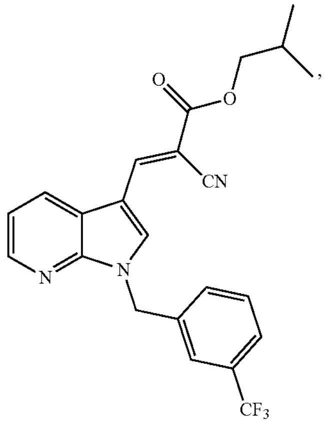
,
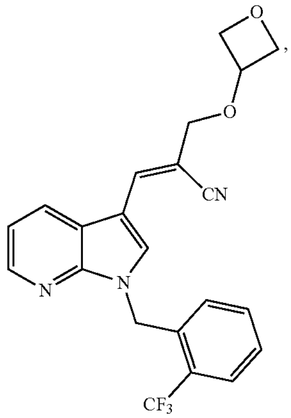
,
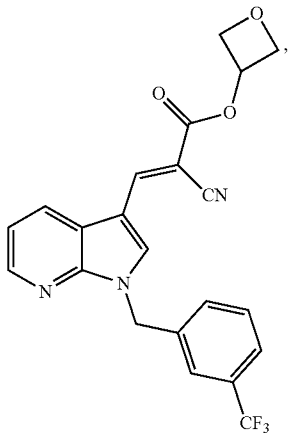
,
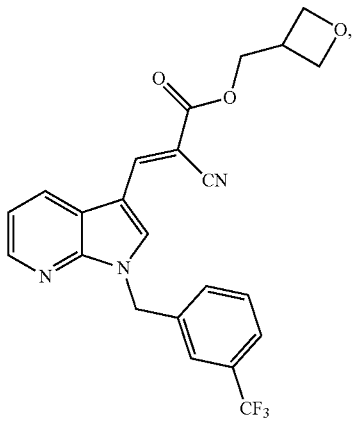
,
-continued
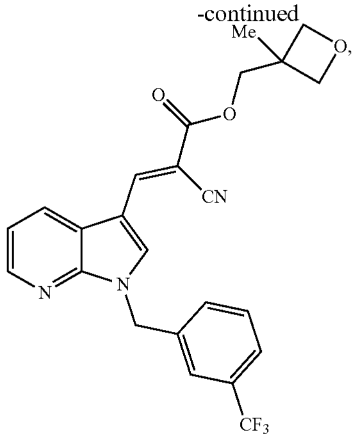
,
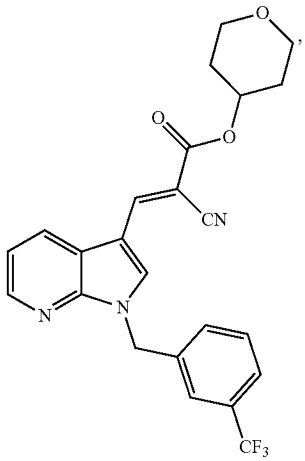
, or
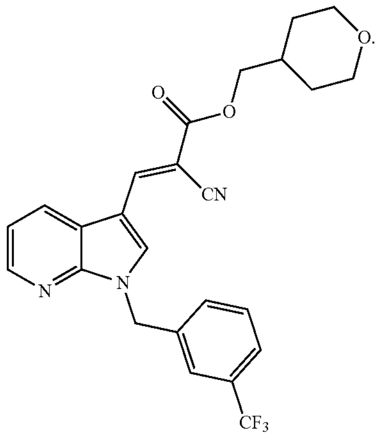
.

In other embodiments, the compound is a compound shown below, each of which may be optionally substituted:

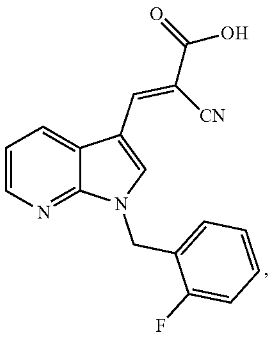

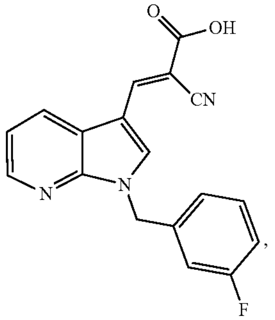

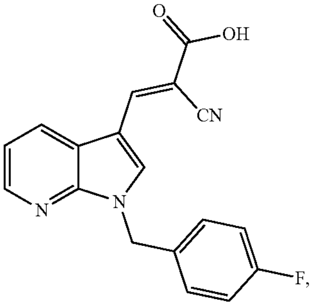

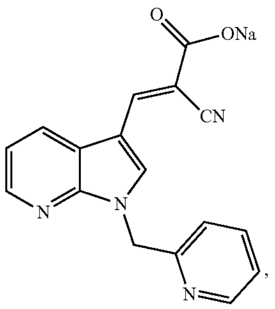

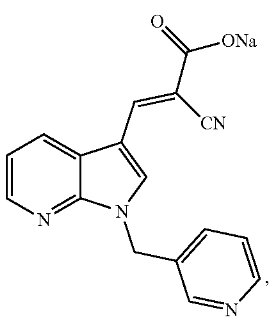

or

-continued

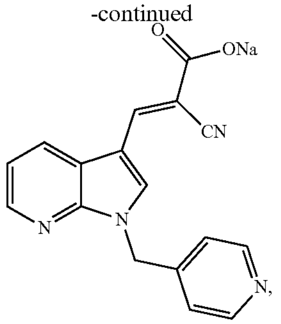

The compound described herein are useful for growing hair. For example, a compound described herein may be administered to the skin of a mammal in the area where hair growth is intended.

For use in growing hair, a compound described herein may be mixed with a dermatologically compatible vehicle or carrier, e.g. so that the compound is present at an amount of about 0.001-10% or about 0.01-2%. The vehicle which may be employed for a topical dermatological composition may comprise, for example, aqueous solutions such as e.g., physiological salines, oil, solutions, ointments, gels, creams, sprays, etc. In some embodiments, the vehicle may contain a solvent such as ethanol or polyethylene glycol. In some embodiments, the vehicle may also contain a penetration enhancer, e.g. to enhance penetration into the skin, such as transcutol P. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity.

Solubility may be important for certain formulations, such as topical formulations, since it may be that more soluble compounds enable delivery of higher concentrations of drug to the target tissues of skin. The solubility of a compound may depend upon the type of formulation. For example, a compound with higher aqueous solubility or polarity May provide higher concentrations of a drug to target tissues when applied with an aqueous, water-soluble, or polar formulation. On the other hand, a compound with higher lipid solubility may provide higher concentrations of a drug to target tissues when applied with an oil-based formulation.

In certain aspects, the compounds of the present disclosure are mitochondrial pyruvate oxidation (MPO) inhibitors. In some embodiments, the compounds described herein may inhibit mitochondrial pyruvate carrier (MPC). In certain embodiments, the MPO inhibitor is an MPC inhibitor. In some aspects, inhibiting MPO in a cell has the effect of enhancing lactate production in a cell and/or enhancing the activity of lactic acid dehydrogenase (LDH) in a cell, and promoting hair growth. In certain aspects, the present disclosure provides methods of promoting hair growth or treating a hair growth condition or disorder such as baldness or alopecia, comprising administering to a patient an MPO inhibitor (e.g., topically, such as with a pharmaceutical composition formulated for topical application), such as a compound of the present disclosure. In certain embodiments, the present disclosure provides methods of promoting hair growth or treating a hair growth condition or disorder such as baldness or alopecia, comprising administering to a patient an MPC inhibitor (e.g., topically, such as with a pharmaceutical composition formulated for topical application), such as a compound of the present disclosure.

In some embodiments, inhibiting the MPO or the MPC in a cell has the effect of enhancing lactate production and/or enhancing the activity of LDH in a cell, and promoting hair growth.

For the purposes of this disclosure, the term "treat," "treating," or a similar term (such as "modulating"), includes cure, mitigation, treatment, or prevention of disease in man or other animals, or any other effect that would be associated with a "drug" as defined under 21 USC 321(g).

In certain aspects, the compounds of the present disclosure may be ester prodrugs. In other aspects, the compounds described herein may be thioester or amide prodrugs. In some embodiments, the compounds herein may show a higher rate of hydrolysis (such as a rate that is at least about 1.1 times higher, at least about 1.5 times higher, at least about 2 times higher, at least about 5 times higher, at least about 10 times higher, at least about 50 times higher, at least about 100 times higher, at least about 500 times higher, at least about 1,000 times higher, at least about 10,000 times higher, about 1.1-2 times higher, about 2-4 times higher, about 4-6 times higher, about 6-8 times higher, about 8-10 times higher, about 1.1-10 times higher, about 10-100 times higher, about 100-1,000 times higher, or about 1,000-10,000 times higher) relative to conventional alkyl (ethyl or methyl) esters. In some aspects, the compounds of the present disclosure may achieve a high level of hydrolyzed drug (carboxylic acid) in skin homogenate assays.

It is understood that topical delivery of an active pharmaceutical ingredient (API) for dermal indications comprises a balance of lipophilic and hydrophilic properties. It is believed that a compound having lipophilicity as a prodrug and hydrophilicity as the corresponding free acid API may achieve the goal of reaching the desired skin layer target (e.g., a hair follicle). The rate of hydrolysis of the prodrug in the layers of the skin may be adjusted to achieve the desired result.

In some embodiments, the compounds of the present disclosure undergo hydrolysis to release the active free carboxylic acid. In some aspects, the compounds of the present disclosure undergo hydrolysis to release the active free carboxylic acid at a rate that is enhanced relative to conventional prodrugs (e.g., JXL082). In some embodiments, the rate of hydrolysis may benefit the delivery of active pharmaceutical agent to potentiate hair growth.

In some aspects, the prodrug compounds of the present disclosure undergo hydrolysis in human skin homogenate faster than known prodrugs such as JXL082. In some embodiments, the concentration of carboxylic acid (API) released by a prodrug of the present disclosure is at least about 150% greater to about 20000% greater than the amount released by a conventional prodrug such as JXL082. In some embodiments, the concentration of carboxylic acid (API) released by a prodrug of the present disclosure is at least about 150-300% greater, about 300-500% greater, about 500-1000% greater, about 1000-2000% greater, about 2000-4000% greater, about 4000-7000% greater, about 7000-10000% greater, about 10000-15000% greater, or about 15000-20000% greater, or about any value in a range bounded by any of these ranges, than the amount released by a conventional prodrug such as JXL082.

In other embodiments, the compounds of the present disclosure may enhance hair growth in their free acid form.

EXAMPLES

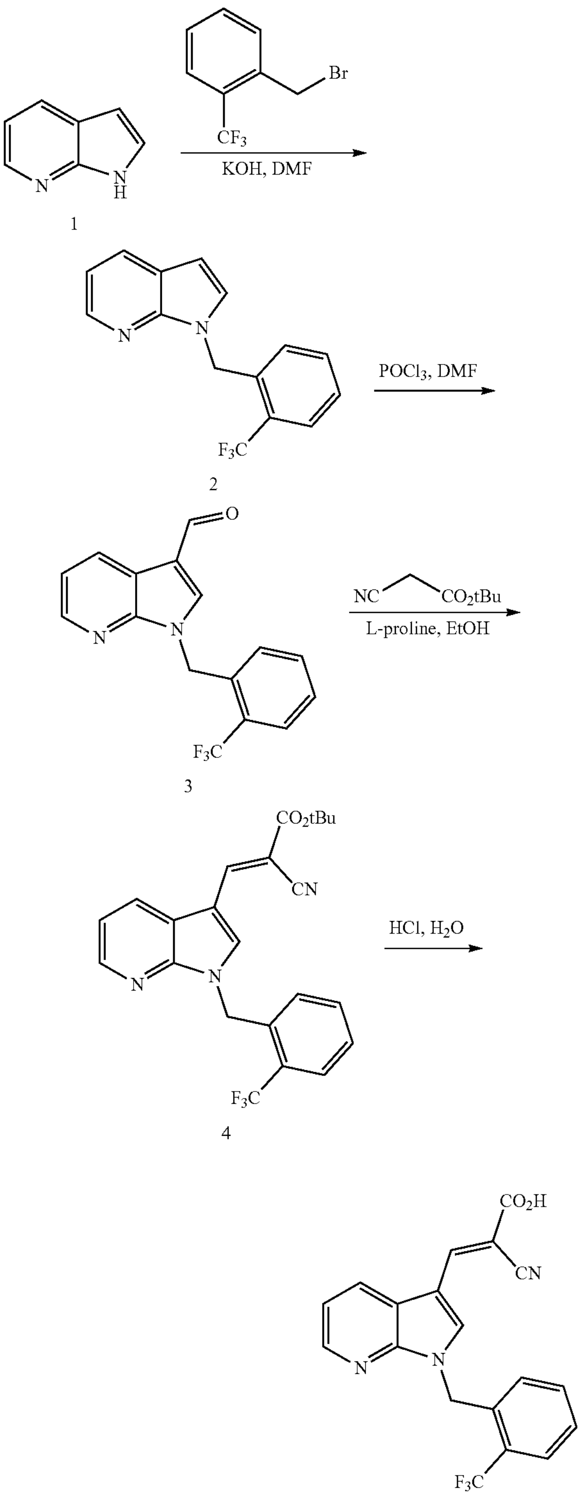

1

2

3

4

PP26

Example 1: (E)-2-Cyano-3-(1-(2-(trifluoromethyl) benzyl)-1H-pyrrolo[2,3-b]pyridin-3-yl) acrylic acid (PP26)

PP26

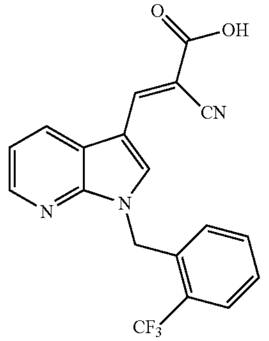

To the solution of compound 1 (1.0 equiv., 2.82 mmol, 332.8 mg) in dry DMF (5.6 mL) were added 2-(trifluoromethyl)benzyl bromide (1.2 equiv., 3.38 mmol, 808.1 mg) and KOH (1.2 equiv., 3.38 mmol, 189.6 mg) at 0° C. The reaction mixture was stirred at 21° C. 8 for 2 h. After the reaction completion shown by TLC, water (5.6 mL) was added to the reaction vial. The reaction mixture was extracted by dichloromethane (14 mL×3). The combined organic layer was dried by sodium sulfate and concentrated. The residue was purified by flash column chromatography (hexanes/EtOAc=12:1) to provide the desired product, compound 2 (yield 89%, 690.3 mg) as a yellow solid.

$POCl_3$ (1 equiv., 2.29 mmol, 213.5 L) was added dropwise to DMF (4.58 mL) at 0° C. under argon. After stirring for 10 min, a solution of compound 2 (1 equiv., 2.29 mmol, 632.2 mg) in DMF (4.58 mL) was added slowly with stirring. The mixture was kept at 21° C. overnight. The reaction was quenched by adding water (4.58 mL) at 0° C., then extracted with dichloromethane (13.74 mL×3). The combined organic layer was dried by sodium sulfate and concentrated. The residue was purified by flash column chromatography (hexanes/EtOAc=4:1) to provide the desired product, compound 3 (yield 79%, 552.1 mg) as a white solid.

To a solution of compound 3 (1.0 equiv., 1.77 mmol, 540.0 mg) in ethanol (7.0 mL) was added tert-butyl 2-cyanoacetate (1.3 equiv., 2.31 mmol, 289.9 μL) and L-proline (40 mol %, 0.71 mmol, 81.7 mg). The reaction was stirred at 21° C. for 12 h and a yellow solid precipitated gradually. After completion of the reaction, ice-cold water (7.0 mL) was added into the reaction vial. The solid was separated by Buchner funnel filtration and washed with water (7.0 mL×3) and dried to afford the desired product, compound 4 (yield 76%, 574.2 mg) as a white solid.

To a solution of compound 4 (1.0 equiv., 2.87 mmol, 1.23 g) was added 12 M aq. HCl (1025.8 equiv., 2942.4 mmol, 245.2 mL) at 0° C. The reaction mixture was stirred at 21° C. for 12 h. After the reaction was complete as shown by TLC, water (500 mL) was added at 0° C. The solid was filtered and washed with water (3×100 mL) then air dried. Finally, the product was dried in vacuo yielding the desired product, PP26 (yield 93%, 986.7 mg) as a light pink solid.

The following compounds were synthesized by a route similar to that described for PP26: PP27, PP28, PP31, PP32, PP33, PP34, PP35, PP36, PP37, PP38, PP39, PP40, PP51, PP52, PP53, PP54.

$^{1}$H NMR (500 MHZ, DMSO-$d_6$) δ 13.50 (br s, 1H), 8.71 (s, 1H), 8.54-8.57 (m, 2H), 8.40 (dd, J=4.7, 1.5 Hz, 1H), 7.81 (d, J=7.6 Hz, 1H), 7.49-7.57 (m, 2H), 7.36 (dd, J=8.0, 4.7 Hz, 1H), 6.86 (d, J=7.6 Hz, 1H), 5.86 (s, 2H).

$^{13}$C NMR (125 MHz, DMSO-$d_6$) δ 164.6, 147.9, 146.0, 145.6, 135.4 (2C), 133.7, 129.2, 128.9, 128.8, 126.8 (q, $^{3}J_{C-F}$=5.6 Hz), 126.6 (q, $^{2}J_{C-F}$=30.3 Hz), 124.8 (q, $^{1}J_{C-F}$=274.0 Hz), 120.0, 119.1, 118.2, 108.7, 96.9, 45.4 (d, $^{4}J_{C-F}$=3.2 Hz).

Example 2: (E)-2-Cyano-3-(1-(3-(trifluoromethyl) benzyl)-1H-pyrrolo[2,3-b]pyridin-3-yl) acrylic acid (PP27)

PP27

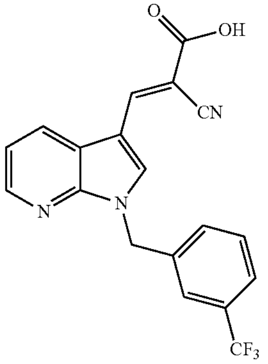

$^{1}$H NMR (500 MHZ, DMSO-$d_6$) δ 13.49 (br s, 1H), 8.81 (s, 1H), 8.50-8.52 (m, 2H), 8.43 (dd, J=4.7, 1.5 Hz, 1H), 7.78 (s, 1H), 7.63-7.65 (m, 1H), 7.55-7.56 (2H), 7.34 (dd, J=8.0, 4.7 Hz, 1H), 5.76 (s, 2H).

$^{13}$C NMR (125 MHz, DMSO-$d_6$) δ 164.7, 147.8, 146.1, 145.5, 138.8, 135.2, 132.2, 130.4, 129.8 (q, $^{2}J_{C-F}$=31.5 Hz), 129.1, 125.1 (q, $^{3}J_{C-F}$=3.8 Hz), 124.9 (q, $^{3}J_{C-F}$=3.9 Hz), 124.5 (q, $^{1}J_{C-F}$=272.3 Hz), 120.0, 119.0, 118.3, 108.5, 96.8, 48.0.

Example 3: (E)-2-Cyano-3-(1-(4-(trifluoromethyl) benzyl)-1H-pyrrolo[2,3-b]pyridin-3-yl)acrylic acid (PP28)

PP28

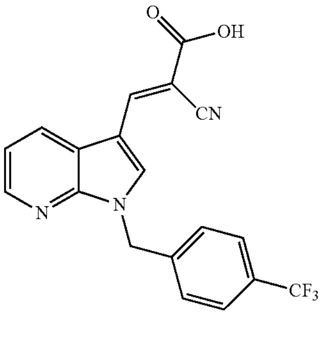

$^{1}$H NMR (500 MHZ, DMSO-$d_6$) δ 13.49 (s, 1H) 8.80 (s, 1H), 8.52-8.54 (m, 2H), 8.42 (dd, J=4.7, 1.5 Hz, 1H), 7.69 (d, J=7.9 Hz, 2H), 7.46-7.48 (m, 2H), 7.35 (dd, J=8.0, 4.7 Hz, 1H), 5.77 (s, 2H).

$^{13}$C NMR (125 MHz, DMSO-$d_6$) δ 164.7, 147.8, 146.1, 145.6, 142.2, 135.3, 129.1, 128.8 (q, $^{2}J_{C-F}$=31.5 Hz), 128.6

(2C), 126.1 (q, $^3J_{C-F}$=3.8 Hz, 2C), 124.6 (q, $_1J_{C-F}$=272.6 Hz), 120.0, 119.1, 118.3, 108.6, 96.7, 48.1.

PP31

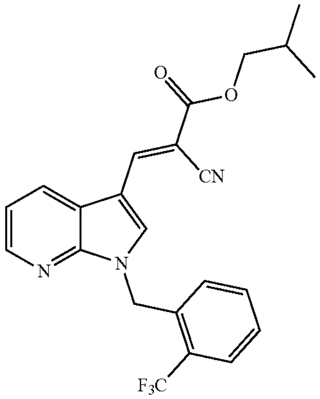

Example 3: Isobutyl (E)-2-cyano-3-(1-(2-(trifluoromethyl)benzyl)-1H-pyrrolo[2,3-b]pyridin-3-yl) acrylate (PP31)

$^1$H NMR (500 MHZ, $CDCl_3$) δ 8.54 (s, 1H), 8.49 (s, 1H), 8.47 (dd, J=4.7, 1.3 Hz, 1H), 8.23 (dd, J=8.0, 1.4 Hz, 1H), 7.74 (dt, J=7.7, 3.7 Hz, 1H), 7.41 (dd, J=5.8, 3.4 Hz, 2H), 7.32 (dd, J=8.0, 4.7 Hz, 1H), 6.90 (dd, J=5.2, 3.6 Hz, 1H), 5.82 (s, 2H), 4.08 (d, J=6.6 Hz, 2H), 2.07 (hept, J=6.7 Hz, 1H), 1.01 (d, J=6.7 Hz, 6H).

$^{13}$C NMR (125 MHz, $CDCl_3$) δ 163.48, 148.01, 145.53, 145.07, 134.38, 133.82, 132.52, 128.53, 128.21, 127.90 (q, $^2J_{C-F}$=32.4 Hz), 127.53, 126.43 (q, $^3J_{C-F}$=5.6 Hz), 124.22 (q, $^1J_{C-F}$=273.6 Hz), 120.10, 118.76, 117.37, 109.03, 96.48, 72.04, 45.26 (d, $^3J_{C-F}$=3.2 Hz), 27.84, 19.02 (2C).

PP32

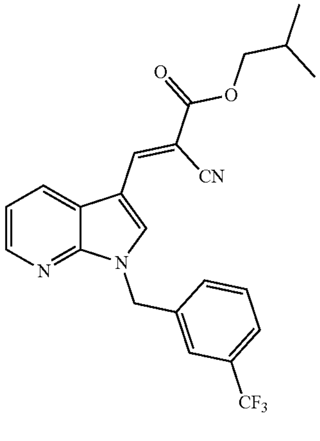

Example 4: Isobutyl (E)-2-cyano-3-(1-(3-(trifluoromethyl)benzyl)-1H-pyrrolo[2,3-b]pyridin-3-yl) acrylate (PP32)

$^1$H NMR (500 MHZ, $CDCl_3$) δ 8.62 (s, 1H), 8.46-8.48 (m, 2H), 8.18 (dd, J=8.0, 1.5 Hz, 1H), 7.59 (s, 1H), 7.55-7.57 (m, 1H), 7.43-7.47 (m, 2H), 7.30 (dd, J=7.9, 4.7 Hz, 1H), 5.63 (s, 2H), 4.08 (d, J=6.7 Hz, 2H), 2.07 (hept, J=6.7 Hz, 1H), 1.01 (d, J=6.7 Hz, 6H).

$^{13}$C NMR (125 MHz, $CDCl_3$) δ 163.4, 147.7, 145.5, 145.1, 136.9, 131.4 (q, $^2J_{C-F}$=32.5 Hz), 130.9, 130.9, 129.6, 127.5, 125.2 (q, $^3J_{C-F}$=3.7 Hz), 124.5 (q, $^3J_{C-F}$=3.8 Hz), 123.8 (q, $_1J_{C-F}$=272.5 Hz), 120.3, 118.7, 117.5, 109.0, 96.4, 72.1, 48.6, 27.8, 19.0 (2C).

PP33

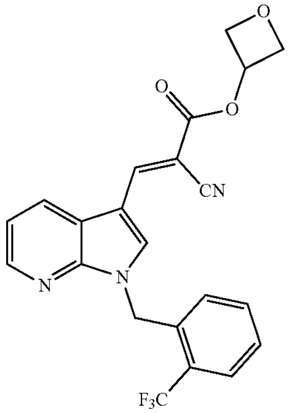

Example 5: Oxetan-3-yl (E)-2-cyano-3-(1-(2-(trifluoromethyl)benzyl)-1H-pyrrolo[2,3-b]pyridin-3-yl) acrylate (PP33)

$^1$H NMR (500 MHZ, $CDCl_3$) δ 8.57 (s, 1H), 8.48-8.50 (m, 2H), 8.23 (dd, J=8.0, 1.5 Hz, 1H), 7.74-7.77 (m, 1H), 7.41-7.44 (m, 2H), 7.34 (dd, J=8.0, 4.7 Hz, 1H), 6.91-6.95 (m, 1H), 5.83 (s, 2H), 5.59-5.64 (m, 1H), 4.94-4.97 (m, 2H), 4.77-4.79 (m, 2H).

$^{13}$C NMR (125 MHZ, $CDCl_3$) δ 162.8, 148.1, 146.1, 145.7, 134.5, 134.2, 132.6, 128.6, 128.3, 127.9 (q, $^2J_{C-F}$=31.6 Hz), 127.6, 126.5 (q, $^3J_{C-F}$=5.7 Hz), 124.2 (q, $_1J_{C-F}$=273.9 Hz), 120.1, 119.0, 117.1, 109.1, 95.0, 69.2 (3C), 45.4 (q, $^4J_{C-F}$=3.1 Hz).

PP34

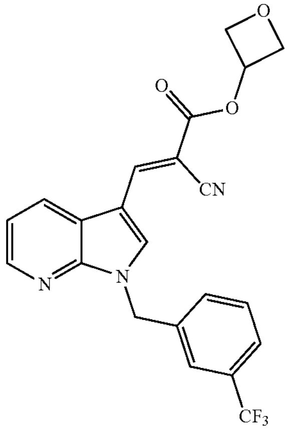

Example 6: Oxetan-3-yl (E)-2-cyano-3-(1-(3-(trifluoromethyl)benzyl)-1H-pyrrolo[2,3-b]pyridin-3-yl) acrylate (PP34)

$^1$H NMR (500 MHZ, $CDCl_3$) δ 8.66 (s, 1H), 8.48-8.49 (m, 2H), 8.19 (dd, J=8.0, 1.5 Hz, 1H), 7.57-7.60 (m, 2H), 7.45-7.48 (m, 2H), 7.33 (dd, J=8.0, 4.7 Hz, 1H), 5.60-5.64 (m, 3H), 4.94-4.97 (m, 2H), 4.77-4.80 (m, 2H).

$^{13}$C NMR (125 MHz, $CDCl_3$) δ 162.7, 147.8, 146.1, 145.7, 136.7, 133.8, 131.4 (q, $^2J_{C-F}$=32.6 Hz), 131.0, 129.6, 127.5, 125.3 (q, $^3J_{C-F}$=3.7 Hz), 124.6 (q, $^3J_{C-F}$=3.8 Hz), 123.7 (q, $^1J_{C-F}$=272.6 Hz), 120.3, 119.0, 117.3, 109.0, 94.9, 69.2 (3C), 48.7.

PP35

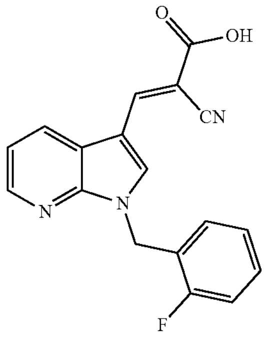

Example 7: (E)-2-cyano-3-(1-(2-fluorobenzyl)-1H-pyrrolo[2,3-b]pyridin-3-yl)acrylic acid (PP35)

$^1$H NMR (500 MHZ, DMSO-d$_6$) δ 13.48 (br s, 1H), 8.72 (s, 1H), 8.50-8.52 (m, 2H), 8.42 (dd, J=4.6, 1.3 Hz, 1H), 7.33-7.38 (m, 2H), 7.23 (t, J=8.8 Hz, 2H), 7.13-7.16 (m, 1H), 5.69 (s, 2H).

$^{13}$C NMR (125 MHz, DMSO-d$_6$) δ 164.7, 160.6 (d, $^1J_{C-F}$=245.8 Hz), 147.8, 146.0, 145.5, 135.1, 130.8 (d, $^3J_{C-F}$=8.2 Hz), 130.7 (d, $^3J_{C-F}$=3.7 Hz), 129.0, 125.2 (d, $^4J_{C-F}$=3.5 Hz), 124.0 (d, $^2J_{C-F}$=14.7 Hz), 120.0, 119.0, 118.4, 116.1 (d, $^2J_{C-F}$=20.9 Hz), 108.4, 96.6, 42.9 (d, $^3J_{C-F}$=3.9 Hz).

PP36

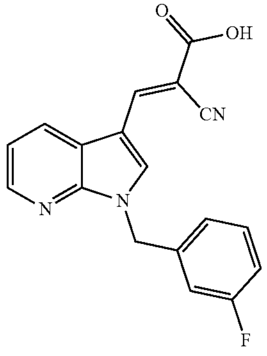

Example 8: (E)-2-cyano-3-(1-(3-fluorobenzyl)-1H-pyrrolo[2,3-b]pyridin-3-yl)acrylic acid (PP36)

$^1$H NMR (500 MHZ, DMSO-d$_6$) δ 13.48 (br s, 1H), 8.76 (s, 1H), 8.50-8.52 (m, 2H), 8.43 (dd, J=4.7, 1.5 Hz, 1H), 7.33-7.39 (m, 2H), 7.09-7.17 (m, 3H), 5.67 (s, 2H).

$^{13}$C NMR (125 MHz, DMSO-d$_6$) δ 164.7, 162.6 (d, $^1J_{C-F}$=244.2 Hz), 147.8, 146.1, 145.5, 140.2 (d, $^3J_{C-F}$=7.3 Hz), 135.2, 131.3 (d, $^3J_{C-F}$=8.4 Hz), 129.1, 124.1 (d, $^4J_{C-F}$=2.7 Hz), 120.0, 119.0, 118.3, 115.1 (d, $^2J_{C-F}$=20.9 Hz), 114.9 (d, $^2J_{C-F}$=21.9 Hz), 108.5, 96.6, 48.0 (d, $^4J_{C-F}$=1.1 Hz).

PP37

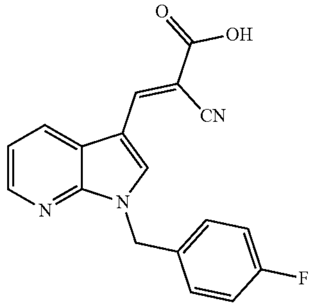

Example 8: (E)-2-cyano-3-(1-(4-fluorobenzyl)-1H-pyrrolo[2,3-b]pyridin-3-yl)acrylic acid (PP37)

$^1$H NMR (500 MHz, DMSO-d$_6$) δ 8.74 (s, 1H), 8.49-8.51 (m, 2H), 8.43 (dd, J=4.7, 1.3 Hz, 1H), 7.39 (dd, J=8.6, 5.5 Hz, 2H), 7.34 (dd, J=8.0, 4.7 Hz, 1H), 7.14-7.17 (m, 2H), 5.63 (s, 2H).

$^{13}$C NMR (125 MHZ, DMSO-d$_6$) δ 164.7, 162.1 (d, $^1J_{C-F}$=243.8 Hz), 147.8, 146.1, 145.5, 135.0, 133.6 (d, $^4J_{C-F}$=3.1 Hz), 130.4 (d, $^3J_{C-F}$=8.3 Hz, 2C), 129.0, 120.0, 119.0, 118.3, 116.0 (d, $^2J_{C-F}$=21.5 Hz, 2C), 108.4, 96.4, 47.8.

PP38

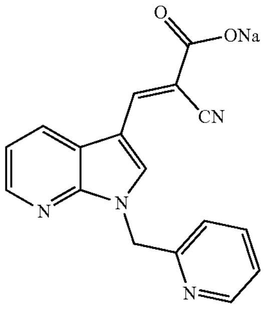

Example 9: Sodium (E)-2-cyano-3-(1-(pyridin-2-ylmethyl)-1H-pyrrolo[2,3-b]pyridin-3-yl)acrylate (PP38)

$^1$H NMR (500 MHz, DMSO-d$_6$) δ 8.80 (s, 1H), 8.47-8.53 (m, 3H), 8.37 (dd, J=4.7, 1.5 Hz, 1H), 7.79 (td, J=7.7, 1.8 Hz, 1H), 7.29-7.34 (m, 3H), 5.77 (s, 2H).

$^{13}$C NMR (125 MHz, DMSO-d$_6$) δ 164.7, 156.0, 149.5, 147.9, 146.1, 145.3, 138.0, 136.1, 128.9, 123.5, 122.4, 120.0, 118.9, 118.4, 108.3, 96.2, 50.0.

PP39

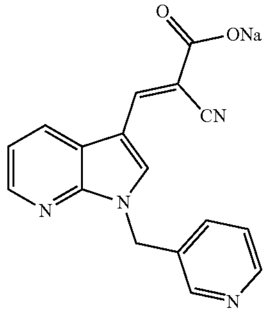

Example 10: Sodium (E)-2-cyano-3-(1-(pyridin-3-ylmethyl)-1H-pyrrolo[2,3-b]pyridin-3-yl)acrylate (PP39)

$^1$H NMR (500 MHZ, DMSO-$d_6$) δ 8.88 (d, J=1.9 Hz, 1H), 8.85 (s, 1H), 8.72 (dd, J=5.4, 1.3 Hz, 1H), 8.51-8.54 (m, 2H), 8.42 (dd, J=4.7, 1.5 Hz, 1H), 8.23 (dt, J=8.1, 1.6 Hz, 1H), 7.79 (dd, J=8.0, 5.4 Hz, 1H), 7.36 (dd, J=8.0, 4.7 Hz, 1H), 5.82 (s, 2H).

$^{13}$C NMR (125 MHz, DMSO-$d_6$) δ 164.6, 147.7, 146.0, 145.5, 144.5, 144.7, 142.3, 135.7, 135.3, 129.2, 126.5, 120.17, 119.2, 118.2, 108.7, 97.0, 45.9.

PP40

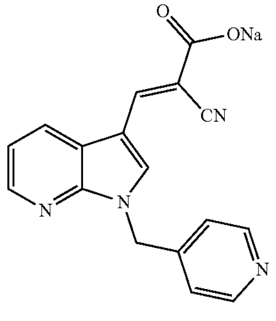

Example 11: Sodium (E)-2-cyano-3-(1-(pyridin-4-ylmethyl)-1H-pyrrolo[2,3-b]pyridin-3-yl)acrylate (PP40)

$^1$H NMR (500 MHZ, DMSO-$d_6$) δ 8.87 (s, 1H), 8.77 (d, J=6.6 Hz, 2H), 8.56 (d, J=9.2 Hz, 1H), 8.55 (s, 1H), 8.38 (d, J=4.7 Hz, 1H), 7.69 (d, J=6.3 Hz, 2H), 7.37 (dd, J=8.0, 4.7 Hz, 1H), 5.98 (s, 2H).

$^{13}$C NMR (125 MHZ, DMSO-$d_6$) δ 164.6, 156.0, 147.7, 145.9, 145.7, 143.8 (2C), 135.4, 129.3, 124.9 (2C), 120.1, 119.3, 118.1, 109.0, 97.4, 48.0.

PP51

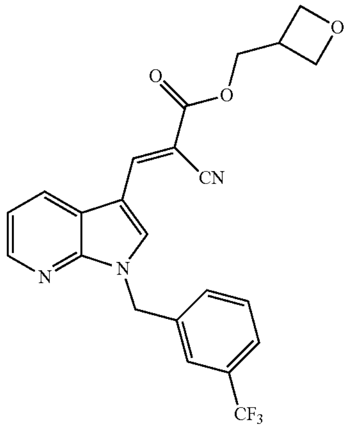

Example 12: Oxetan-3-ylmethyl (E)-2-cyano-3-(1-(3-(trifluoromethyl)benzyl)-1H-pyrrolo[2,3-b]pyridin-3-yl)acrylate (PP51)

$^1$H NMR (500 MHZ, $CDCl_3$) δ 8.61 (s, 1H), 8.48 (d, J=0.8 Hz, 1H), 8.47 (dd, J=4.7, 1.5 Hz, 1H), 8.17 (dd, J=7.9, 1.5 Hz, 1H), 7.59 (s, 1H), 7.54-7.56 (m, 1H), 7.44 (d, J=5.3 Hz, 2H), 7.30 (dd, J=8.0, 4.7 Hz, 1H), 5.62 (s, 2H), 4.85 (dd, J=7.8, 6.4 Hz, 2H), 4.51-4.55 (m, 4H), 3.36-3.45 (m, 1H).

$^{13}$C NMR (125 MHz, $CDCl_3$) δ 163.4, 147.7, 145.6, 145.6, 136.8, 133.5, 131.4 (q, $^2J_{C-F}$=33.4 Hz), 131.0, 129.6, 127.5, 125.2 (q, $^3J_{C-F}$=3.8 Hz), 124.6 (q, $^3J_{C-F}$=3.8 Hz), 123.8 (q, $^1J_{C-F}$=272.8 Hz), 120.3, 118.9, 117.4, 109.0, 95.6, 74.0 (2C), 66.8, 48.6, 34.2.

PP52

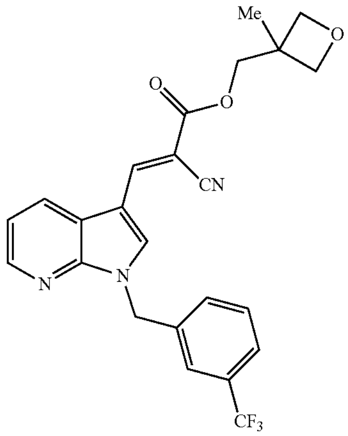

Example 13: (3-methyloxetan-3-yl)methyl (E)-2-cyano-3-(1-(3-(trifluoromethyl)benzyl)-1H-pyrrolo[2,3-b]pyridin-3-yl)acrylate (PP52)

$^1$H NMR (500 MHz, $CDCl_3$) δ 8.62 (s, 1H), 8.50 (s, 1H), 8.47 (dd, J=4.7, 1.4 Hz, 1H), 8.17 (dd, J=8.0, 1.4 Hz, 1H), 7.59 (s, 1H), 7.55-7.56 (m, 1H), 7.44 (d, J=5.2 Hz, 2H), 7.30 (dd, J=7.9, 4.7 Hz, 1H), 5.63 (s, 2H), 4.57 (d, J=6.1 Hz, 2H), 4.44 (d, J=6.1 Hz, 2H), 4.41 (s, 2H), 1.41 (s, 3H).

$^{13}$C NMR (125 MHz, $CDCl_3$) δ 163.4, 147.7, 145.6 (2C), 136.9, 133.5, 131.3 (q, $^2J_{C-F}$=31.5 Hz), 131.0, 129.6, 127.4, 125.2 (q, $^3J_{C-F}$=3.8 Hz), 124.6 (q, $^3J_{C-F}$=3.8 Hz), 123.8 (q, $^1J_{C-F}$=272.8 Hz), 120.3, 118.9, 117.3, 109.0, 95.6, 79.5 (2C), 70.2, 48.6, 39.4, 21.0.

PP53

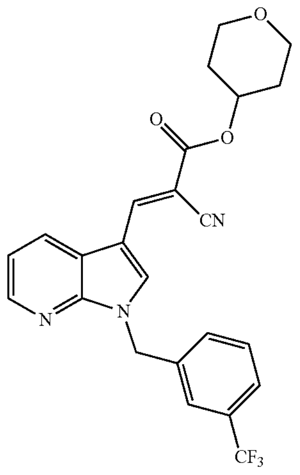

Example 14: Tetrahydro-2H-pyran-4-yl (E)-2-cyano-3-(1-(3-(trifluoromethyl)benzyl)-1H-pyrrolo[2,3-b]pyridin-3-yl)acrylate (PP53)

$^1$H NMR (500 MHZ, $CDCl_3$) δ 8.62 (s, 1H), 8.45-8.47 (m, 2H), 8.16 (dd, J=8.0, 1.5 Hz, 1H), 7.59 (s, 1H), 7.54-7.56 (m, 1H), 7.42-7.46 (m, 2H), 7.29 (dd, J=7.9, 4.7 Hz, 1H), 5.62 (s, 2H), 5.14 (hept, J=4.2 Hz, 1H), 3.96 (ddd, J=11.9, 6.0, 3.8 Hz, 2H), 3.59 (ddd, J=11.7, 8.3, 3.2 Hz, 2H), 1.97-2.03 (m, 2H), 1.80-1.85 (m, 2H).

$^{13}$C NMR (125 MHZ, $CDCl_3$) δ 162.7, 147.7, 145.5, 145.2, 136.9, 133.3, 131.4 (q, $^2J_{C-F}$=33.4 Hz), 130.9, 129.6, 127.4, 125.2 (q, $^3J_{C-F}$=3.8 Hz), 124.5 (q, $^3J_{C-F}$=3.8 Hz), 123.8 (q, $^1J_{C-F}$=272.3 Hz), 120.3, 118.8, 117.5, 109.0, 96.4, 71.0, 65.1 (2C), 48.6, 31.6 (2C).

PP54

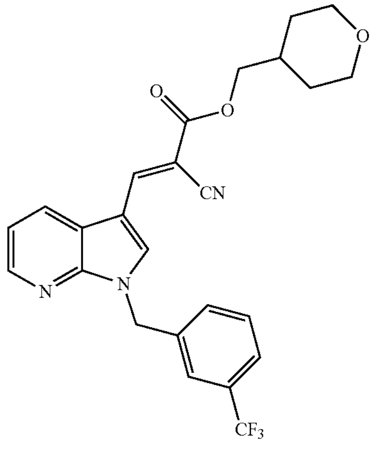

Example 15: (tetrahydro-2H-pyran-4-yl)methyl (E)-2-cyano-3-(1-(3-(trifluoromethyl)benzyl)-1H-pyrrolo[2,3-b]pyridin-3-yl)acrylate (PP54)

$^1$H NMR (500 MHz, $CDCl_3$) δ 8.61 (s, 1H), 8.45-8.47 (m, 2H), 8.17 (dd, J=8.0, 1.5 Hz, 1H), 7.59 (s, 1H), 7.54-7.56 (m, 1H), 7.44-7.45 (m, 2H), 7.30 (dd, J=7.9, 4.7 Hz, 1H), 5.62 (s, 2H), 4.15 (d, J=6.7 Hz, 2H), 3.99 (dd, J=11.3, 3.0 Hz, 2H), 3.41 (td, J=11.9, 2.1 Hz, 2H), 1.99-2.08 (m, 1H), 1.70 (dd, J=12.8, 1.8 Hz, 2H), 1.42 (qd, J=12.0, 4.5 Hz, 2H).

$^{13}$C NMR (125 MHZ, $CDCl_3$) δ 163.4, 147.72, 145.5, 145.3, 136.9, 133.3, 131.4 (q, $^2J_{C-F}$=33.4 Hz), 130.9, 129.6, 127.5, 125.2 (q, $^3J_{C-F}$=3.8 Hz), 124.5 (q, $^3J_{C-F}$=3.8 Hz), 123.8 (q, $^1J_{C-F}$=272.8 Hz), 120.3, 118.8, 117.5, 109.0, 96.0, 70.1, 67.4 (2C), 48.6, 34.6, 29.4 (2C).

Testing Methods

Example 15

Solubility Testing:

The solubility of the compounds prepared as described above was tested in a formulation containing about 25-75% polyethylene glycol, about 5-20% transcutol, about 5-50% ethanol, and about 5-10% DMSO. Results are detailed in the table below.

| Compound ID | Conc. | Notes |
|---|---|---|
| JXL069 | 0.027% w/w | Stirred overnight at room temperature; dissolved |
| PP26 | 0.1% w/w | Stirred 1 hour at room temperature; dissolved |
| PP27 | 0.15% w/w | Stirred 1 hour at room temperature; dissolved |
| PP35 | 0.1% w/w | Stirred 24 hours at room temperature; failed to dissolve |
| PP36 | 0.1% w/w | Stirred 24 hours at room temperature; failed to dissolve |
| PP55 | 0.4% w/w | Stirred 1 hour at room temperature; dissolved. Slightly opaque at 1.0% w/w |
| PP56 | 0.1% w/w | Stirred 24 hours at room temperature; failed to dissolve |
| PP57 | 0.3% w/w | Stirred 1 hour at room temperature; dissolved |

Example 16

General Information

The study was designed to test Mitochondrial Pyruvate Carrier (MPC) by measuring respiration driven through Complex I of the electron transport chain using pyruvate as a substrate. Permeabilized HepG2 cells were acutely treated with test compounds in a nine-point dose-response. Permeabilizing the cells allowed for direct testing of pyruvate oxidation, which requires pyruvate transport into the mitochondria through the MPC. Oxygen consumption was evaluated using the XF96 platform by measuring oxygen consumption rates (OCR) in the presence of ADP to measure maximal ATP synthesis capacity (State 3) and in the presence of FCCP to determine maximal substrate oxidation (uncoupled respiration). UK5099, an MPC inhibitor, was used as a positive control to inhibit mitochondrial pyruvate oxidation.

HepG2 Cells

HepG2 cells were cultured in the DMEM medium supplemented with 5.5 mM glucose, 4 mM glutamine, 1 mM pyruvate, and 10% FBS. HepG2 cells were plated in poly-d-lysine-coated XF96 microplates at 8,000 cells per well and maintained in a cell culture incubator overnight (37° C. incubator with 5% $CO_2$). On the day of the assay, test compounds were prepared in MAS buffer (70 mM sucrose, 220 mM mannitol, 5 mM potassium phosphate, 5 mM magnesium chloride, 1 mM EGTA, and 2 mM HEPES, pH 7.2 adjusted with KOH) containing 2× pyruvate (10 mM), malate (1 mM), ADP (8 mM), and recombinant, mutant perfringolysin O (PFO; XF PMP; Agilent Technologies; 10 nM) to permeabilize the plasma membrane. The cells were washed twice with MAS and then 75 µL of 2× compound, pyruvate, malate, ADP, and PFO was added to cells in 75 µL of MAS. The cells were incubated in a 37° C. incubator without $CO_2$ for 10 minutes before loading the plate into the XF96 Analyzer.

The injection ports of the XF96 Assay Cartridge were loaded with compounds that target the electron transport chain, which were injected during the assay. The assay included sequential injection of:

(a) The ATP Synthase inhibitor, oligomycin;

(b) The chemical uncoupler, FCCP, to release the control of mitochondrial ATP synthesis over respiration and determine maximal respiratory capacity under pyruvate; and (c) Complex I inhibitor, rotenone, and Complex III inhibitor, antimycin A, to halt all mitochondrial respiration No compound washout period occurred before injection of the compounds. The following table summarizes the order in which compounds were injected, the injection volume and concentration, as well as the final concentration of the compounds in the well to which the HepG2 cells were exposed.

| Port | Compound | Injection Volume | Injected Concentration | Final Concentration |
|---|---|---|---|---|
| A | Oligomycin | 25 µL | 14 µM | 2 µM |
| B | FCCP | 25 µL | 8 µM | 1 µM |
| C | FCCP | 25 µL | 8 µM | 1.8 µM |
| D | Rot/Anti A | 25 µL | 20 µM | 2 µM |

Approximately 30 minutes before the end of the assay medium incubation, the XF96 Assay Cartridge was calibrated. Once the calibration process was completed, the microplate was placed into the instrument to begin the assay. The XF96 Extracellular Flux Analyzer 22 protocol for HepG2 cells was as follows:

| Command | Time (minutes) | Port | Repeat |
|---|---|---|---|
| Calibrate | | 30 | |
| Mix | 2 | | 4 |
| Measue | 3 | | |
| Inject | | A (oligomycin) | |
| Mix | 2 | | 2 |
| Measure | 3 | | |
| Inject | | B (FCCP) | |
| Mix | 2 | | 2 |
| Measure | 3 | | |
| Inject | | C (FCCP) | |
| Mix | 2 | | 2 |
| Measure | 3 | | |
| Inject | | D (Rotenone/Antimycin A) | |
| Mix | 2 | | 3 |
| Measure | 3 | | |
| | End Program | | |

Normalization

Upon completion of each respirometry assay, the XF96 microplate was removed from the Seahorse Extracellular Flux Analyzer and fixed with 4% paraformaldehyde. After fixation, the cells were stained with 10 µg/mL Hoechst and cell number per well was assessed with an Operetta High-Content Imaging System. The respirometry well level data (pmoles $O_2$/min) was normalized per cell number (pmoles $O_2$/min/$10^3$ cells) in each assay.

Data Analysis

Each compound was run in duplicate and the average value of State 3 respiration and uncoupled respiration was calculated. Non-mitochondrial respiration (lowest value after injection of antimycin A and rotenone) was subtracted from all rates prior to calculating State 3 and uncoupled respiration. State 3 respiration was calculated as the average of the last 3 OCR measurements before injection of oligomycin in Port A. Uncoupled respiration was measured as the highest OCR after injection of FCCP. The $IC_{50}$ was calculated in Prism GraphPad by plotting the log concentration on the x-axis and OCR on the y-axis.

| Compound | Mean IC50 (nM) | Replicates |
|---|---|---|
| UK5099 | 33.9 | 3 |
| JXL069 | 51.2 | 3 |
| PP26 | 54.0 | 3 |
| PP27 | 36.3 | 3 |
| PP35 | 34 | 1 |
| PP36 | 26 | 1 |
| PP37 | 109 | 1 |
| PP38 | 183 | 1 |
| PP39 | 262 | 1 |
| PP40 | 411 | 1 |

Figure 2:
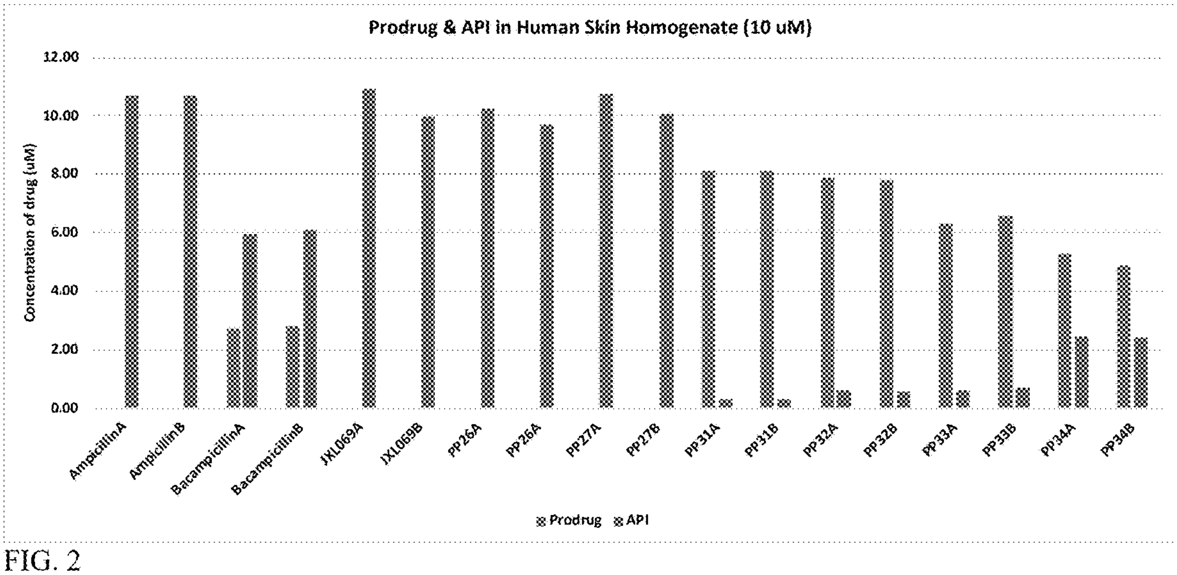
FIG. 2 shows the conversion of ester prodrug (shown in gray) to the corresponding carboxylic acid API (shown in black) after 1 hour of incubation in homogenized human skin at 37° C. and pH 7.4.

Example 17: Measurement of Esterase Activity of Selected Compounds in Human Skin Homogenate Samples of PP31, PP32, PP33, PP34, PP51, PP52, PP53, PP54, and references bacampicillin, ampicillin, JXL069, PP26, PP27 were prepared at a concentration of 10 µM, and incubated with homogenized human skin (0.5 mg/mL) in PBS (saline) solution (total volume of 1 mL) for 1 hour at 37° C. The samples were then quenched with UK5099 and analysis was performed using LCMS. Results are shown in FIGS. 1-2.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein may be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A compound represented by a formula:

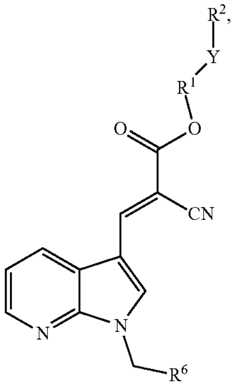

or a pharmaceutically acceptable salt thereof;

wherein $R^1$ is -, —S(=O)$_2$—, an optionally substituted $C_{1-12}$ hydrocarbon group or an optionally substituted heterocycle;

$R^2$ is H, an optionally substituted $C_{1-6}$ alkyl, an optionally substituted carbocycle, or an optionally substituted heterocycle;

Y is —, —O—, 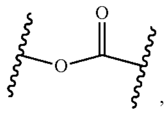 ,

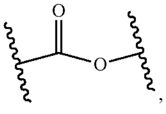 , or 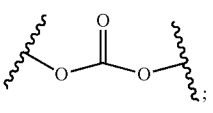 ;

and $R^6$ is:

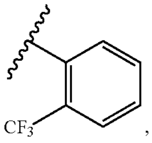 , 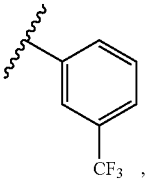 , or

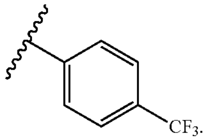

2. The compound of claim 1, wherein $R^6$ is:

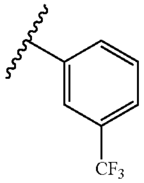 or 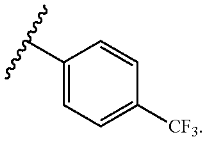

3. The compound of claim 1, wherein $R^1$ is -, —$CH_2$—, an optionally substituted $C_{3-12}$ hydrocarbon group, or an optionally substituted heterocycle having a carbon atom directly attached to the O atom.

4. The compound of claim 1, wherein $R^1$ is an optionally substituted $C_{1-12}$ alkyl.

5. The compound of claim 1, wherein $R^1$ is an optionally substituted heterocycle.

6. The compound of claim 1, wherein $R^1$ is an optionally substituted aryl.

7. The compound of claim 1, wherein $R^1$ is an optionally substituted benzyl.

8. The compound of claim 1, wherein $R^1$ is an optionally substituted oxetane, optionally substituted dihydrofuran, optionally substituted furan, optionally substituted furanone, optionally substituted tetrahydropyran, optionally substituted dihydropyran, optionally substituted pyran, optionally substituted tetrahydropyrone, optionally substituted dihydropyrone, optionally substituted thietane, optionally substituted tetrahydrothiophene, optionally substituted dihydrothiophene, optionally substituted thiophene, optionally substituted azetidine, optionally substituted pyrrolidine, optionally substituted pyrroline, optionally substituted pyrrole, optionally substituted piperidine, optionally substituted pyridine, optionally substituted oxazole, optionally substituted isoxazole, optionally substituted thiazole, optionally substituted isothiazole, optionally substituted pyrazolidine, optionally substituted imidazolidine, optionally substituted pyrazole, optionally substituted imidazole, optionally substituted tetrazole, or optionally substituted sulfolane.

9. The compound of claim 1, wherein Y is -.

10. The compound of claim 1, wherein Y is —O—.

11. The compound of claim 1, wherein Y is

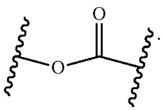 [SMILES: *OC(*)=O]

12. The compound of claim 1, wherein Y is

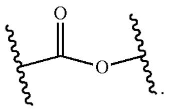 [SMILES: *OC(*)=O]

13. The compound of claim 1, wherein Y is

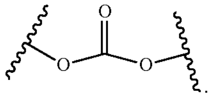 [SMILES: *OC(=O)O*]

14. The compound of claim 1, wherein $R^2$ is H.

15. The compound of claim 1, wherein the compound is

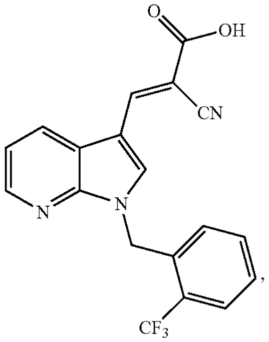 [SMILES: N#C/C(=C\c1cn(Cc2ccccc2C(F)(F)F)c2ncccc12)C(=O)O]

or a pharmaceutically acceptable salt thereof.

16. The compound of claim 1, wherein the compound is

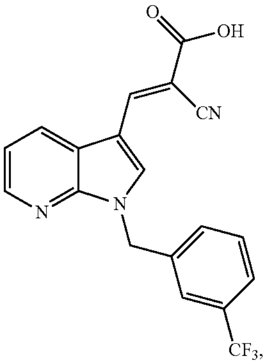 [SMILES: N#C/C(=C\c1cn(Cc2cccc(C(F)(F)F)c2)c2ncccc12)C(=O)O]

or a pharmaceutically acceptable salt thereof.

17. The compound of claim 1, wherein the compound is

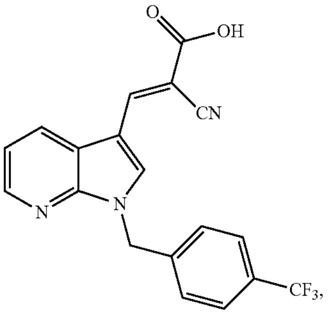 [SMILES: N#C/C(=C\c1cn(Cc2ccc(C(F)(F)F)cc2)c2ncccc12)C(=O)O]

or a pharmaceutically acceptable salt thereof.

18. A pharmaceutical composition comprising a compound of claim 1 and a pharmaceutically acceptable excipient.

* * * * *